(12) United States Patent
Zhang

(10) Patent No.: US 11,952,439 B2
(45) Date of Patent: Apr. 9, 2024

(54) SURFACE GRADIENT CROSS-LINKING METHOD OF ULTRA-HIGH MOLECULAR WEIGHT POLYETHYLENE AND THE APPLICATION THEREOF

(71) Applicants: b-ONE Medical (Suzhou) Co., Ltd., Jiangsu (CN); b-ONE Medical Biotech Corporation, Wuxi (CN); b-ONE Ortho, Corp, Cedar Knolls, NJ (US)

(72) Inventor: Zongtao Zhang, Cedar Knolls, NJ (US)

(73) Assignees: b-ONE Medical (Suzhou) Co., Ltd., Jiangsu (CN); b-ONE Medical Biotech Corporation, Wuxi (CN); b-ONE Orth, Corp, Cedar Knolls, NJ (US)

( * ) Notice: Subject to any disclaimer, the term of this patent is extended or adjusted under 35 U.S.C. 154(b) by 510 days.

(21) Appl. No.: 16/911,831

(22) Filed: Jun. 25, 2020

(65) Prior Publication Data

US 2022/0002452 A1    Jan. 6, 2022

(51) Int. Cl.
| | | |
|---|---|---|
| *C08F 110/02* | (2006.01) | |
| *A61K 31/355* | (2006.01) | |
| *A61L 27/16* | (2006.01) | |
| *A61L 27/54* | (2006.01) | |

(52) U.S. Cl.
CPC .......... *C08F 110/02* (2013.01); *A61K 31/355* (2013.01); *A61L 27/16* (2013.01); *A61L 27/54* (2013.01); *A61L 2430/24* (2013.01); *C08F 2500/01* (2013.01); *C08F 2810/20* (2013.01)

(58) Field of Classification Search
CPC ................ C08F 110/02; C08F 2500/01; C08F 2810/20; A61K 31/355; A61L 27/16; A61L 27/54; A61L 2430/24
See application file for complete search history.

(56) References Cited

U.S. PATENT DOCUMENTS

| | | | |
|---|---|---|---|
| 5,414,049 A | 5/1995 | Sun et al. | |
| 6,494,917 B1 | 12/2002 | McKellop et al. | |
| 7,517,919 B2 | 4/2009 | Wang et al. | |
| 9,132,209 B2 | 9/2015 | He et al. | |
| 9,828,474 B2 | 11/2017 | He et al. | |
| 9,951,190 B2 | 4/2018 | He et al. | |
| 2015/0322239 A1* | 11/2015 | He | A61L 27/16 522/46 |
| 2015/0376349 A1 | 12/2015 | He et al. | |
| 2016/0215117 A1 | 7/2016 | Muratoglu et al. | |
| 2016/0250779 A1 | 9/2016 | Muratoglu et al. | |

FOREIGN PATENT DOCUMENTS

CN            102276864 B         6/2013

OTHER PUBLICATIONS

Chen et al., J. Polymer Science: Part A: Polymer Chemistry, vol. 27, 4051-4075 (1989). (Year: 1989).*
J. Caitlin Huot, et al., "The effect of radiation dose on the tensile and impact toughness of highly crosslinked and remelted ultrahigh-molecular weight polyethylenes", Journal of Biomedical Material Research, May 2011, vol. 97B, No. 2, p. 327-333, cited in Specification.
Ebru Oral, et al., "Surface Cross-Linked UHMWPE Can Enable the Use of Larger Femoral Heads in Total Joints", Journal of Orthopaedic Research, Jan. 2013, p. 59-66, cited in Specification.
Designation F 2977-13, "Standard Test Method for Small Punch Testing of Polymeric Biomaterials Used in Surgical Implants", ASTM International, West Conshohocken, PA, 2013, www.astm.org, published Aug. 2013, cited in Specification.
Jacob Blitz et al., "FEA based DOE study solves specimen slippage in thin film small punch test of highly crosslinked UHMWPE", ORS 2016 Annual Meeting Poster No. 1966, cited in Specification.
Yu Lei Dong, et al., "Ceramics on Ceramics or Ceramics-on-polyethylene for Total Hip Arthroplasty: A Systemic Review and Meta-analysis of Prospective Randomized Studies". Chinese Medical Journal, May 5, 2015, vol. 128, Issue 9, 01223-1231, cited in Specification.
Jörn Reinders, et al., "Wear Performance of Ceramics-On-Metal Hip Bearings", PLoS ONE, www.plosone.org, Aug. 2013, vol. 8, Issue 8, p. 1-7, cited in Specification.
Korduba LA, et al., "Method for creating abrasive components for wear testing", Poster No. 2290, 55th Anneal meeting of the Orthopedic Research Society, cited in Specification as early as Jun. 2020.
International Search Report and Written Opinion issued in PCT/CN2020/127068, dated Mar. 24, 2021, 5 pages provided.

* cited by examiner

*Primary Examiner* — Robert S Cabral
(74) *Attorney, Agent, or Firm* — HSML P.C.

(57) ABSTRACT

The invention relates to a surface gradient cross-linked method of a ultra-high molecular weight polyethylene and the application thereof. The surface gradient crosslinked method of ultrahigh molecular weight polyethylene includes a n ultra-high molecular weight polyethylene surface photoinitiator diffusion step and an ultraviolet light irradiation crosslinking step. In this method, the photoinitiator is diffused deeply into the surface of ultra-high molecular weight polyethylene, the body material shows a gradient cross-linking from the surface to the inside after ultraviolet irradiation so that the whole bulk has a high toughness and the surface there of has a high wear resistance.

15 Claims, 6 Drawing Sheets

SURFACE GRADIENT CROSS-LINKING METHOD OF ULTRA-HIGH MOLECULAR WEIGHT POLYETHYLENE AND THE APPLICATION THEREOF

FIELD

The invention relates to polymer materials, in particular to a surface gradient crosslinking method of ultrahigh molecular weight polyethylene and the application thereof.

BACKGROUND

At present, bulk cross-linking has been commonly used commercially as crosslinking method of ultrahigh molecular weight polyethylene for artificial joints.

Bulk cross-linking is a physical crosslinking method in which the whole bulk is crosslinked through a specific energy ionizing radiation rays. Ionized rays include γ-rays, β-rays, x-rays, and e-beam radiation. The advantage of this cross-linking method is that it can improve the wear resistance of the material by side chain crosslinking of polyethylene molecules. The disadvantage is that this method will also cut off the main chain, resulting in reduced toughness. High wear resistance and high toughness can not be achieved without sacrifice one or another (Reference 1). The whole bulk is too brittle to practically use when the cross-linking degree exceeds 100 kGy (the highest crosslinking degree currently in the orthopedic commercial field is about 100 kGy).

There is also a surface crosslinking ultra-high molecular weight polyethylene (UHMWPE), (References 2-6 and 16). The advantage is that the crosslinking is only carried out in the surface layer, the bulk maintains low-degree cross-linked or non-crosslinked, and both wear resistance and toughness can be compromised. The surface crosslinking can be physical crosslinking or chemical crosslinking. Several patents have been published since the first publication of surface crosslinking patent since year 2000. The Reference 2, for example, employed peroxide chemical cross-linking or low energy e-beam physical crosslinking of pure ultra-high molecular weight polyethylene. The surface of ultra-high molecular weight polyethylene was oxidized using the two methods of Reference 2, so the oxidized surface layer must be removed. However, the result of removing the oxidized surface layer is that the wear resistance is not as good as the bulk crosslinked polyethylene with crosslinking degree of 100 kGy. Reference 3 introduced a large amount of antioxidants (1-2 wt %) into the bulk and reduced the amount of antioxidants on the surface, then applied a large dose of e beam radiation (300 kGy) to achieve the surface and bulk crosslinking. The method overcame the shortcomings of polyethylene surface oxidation, the large amount of antioxidants used in this method also makes the polyethylene substrate soft, bulk crosslinking also makes the material brittle, and high-dose e-beam radiation made the crosslinking too costly.

References (4-6) applied gamma rays to pre-crosslinked ultra-high molecular weight polyethylene on the whole, then coating the photoinitiator which caused crosslinking reaction of polyethylene under ultraviolet light catalysis. The method is a chemical crosslinking. The crosslinking process is to immerse the pre-crosslinked ultra-high molecular weight polyethylene coated with photoinitiator in 65° C. warm water, using low intensity (50 mW/cm$^2$) ultraviolet light at about 350 nm average wavelength, achieved surface crosslinking. The energy of long-wave ultraviolet light (about 350 nanometers) is very low and does not produce an ionization effect, ultraviolet light itself cannot crosslink polyethylene. There are two embodiments of this method. In one embodiment, X3® was used as the bulk material and then conducted surface crosslinking. It showed good surface wear resistance. X3®, a trademark of Stryker, is a highly crosslinked ultra-high molecular weight polyethylene, crosslinked by 30 kGy gamma rays and annealed 3 times. But the disadvantage is that the bulk is highly crosslinked and the whole bulk becomes brittle. In another embodiment, Ultra-high molecular weight polyethylene (trademark N2Vac®) crosslinked with about 30 kGy γ-rays was used as the bulk, then conducted surface crosslinking, showing good bulk toughness. The bearing surface was wear tested against the smooth cobalt-chromium alloy and the surface of PEEK respectively, showing good wear resistance too. The disadvantage is that the depth of crosslinking is unclear. The depth depends on the immersion period of ultra-high molecular weight polyethylene in the photoinitiator solution. Although the claims described a crosslinking depth of 0.2-1.0 mm, no experimental data were provided. References 4-6 mentioned a method of applying a photoinitiator to the surface of ultra-high molecular weight polyethylene by vapor deposition, but it is not supported by embodiments. There is a risk that the crosslinked layer of the polyethylene surface is worn out when the cobalt-chromium alloy ball head becomes rough after a period of clinical use.

In summary, the surface crosslinking method can meet the requirements of both high wear resistance and good toughness, which is theoretically superior to the bulk crosslinking method. However, the disclosed surface crosslinked ultra-high molecular weight polyethylene has shortcomings that have not been overcome, so it has not been commercialized yet. At present, the artificial joint with the lowest clinical wear rate is ceramics to ceramics. The alumina ceramics toughened by zirconia (Delta® ceramics) were wear tested against each other in the hip joint testing machine, and the volume wear rate is 0.118±0.036 mm$^3$/10$^6$ cycles, and its clinical wear rate cannot be tested (References 10-11). When the commercial standard high crosslinked ultra-high molecular weight polyethylene balls (X3®) were wear tested against alumina ceramics toughened by zirconia, the clinical volume wear rate is 29.61 mm$^3$/10$^6$ cycles and the linear wear rate is 0.1 mm/year. The abrasion caused by the liner wear rate of 0.1 mm/year just reached the limit of osteolysis (Reference 12). The disadvantages of ceramics to ceramics, however, are noise, brittle materials and expensive cost. The disadvantage of highly cross-linked ultra-high molecular weight polyethylene is its brittleness, and it has a relative higher wear rate of 0.15 mm/year when wear tested against cobalt-chromium alloy (Reference 13).

Therefore, a super wear-resistant ultra-high molecular weight polyethylene is clinically needed; it should have the same wear resistance as ceramics, but no noise of ceramics-to-ceramics, and it should have as good toughness as traditional ultra high molecular weight polyethylene.

SUMMARY

The present invention is to meet the above clinical needs, by overcoming the shortcomings of the existing surface crosslinking ultra-high molecular weight polyethylene and providing an ultra-high molecular weight polyethylene with more wear-resistant surface and a higher bulk toughness than the pre-arts.

In order to achieve the above goals, this invention provides the following technical solutions:

The first aspect of the present invention provides a crosslinking method for the surface layer of an ultra-high molecular weight polyethylene substrate, the crosslinking method includes the following steps:

(1) diffusing the photoinitiator from the surface of the substrate into the surface layer of the ultra-high molecular weight polyethylene substrate at a temperature above the melting point of the photoinitiator and below the melting point of the ultra high molecular weight polyethylene.

(2) exposing the diffused surface layer with ultraviolet light so that the surface is crosslinked, thereby forming a ultrahigh molecular weight polyethylene with the gradient crosslinked surface layer.

In another preferred embodiment, the ultra-high molecular weight polyethylene substrate is non-ionized crosslinking ultra high molecular weight polyethylene.

In another preferred embodiment, the steps (1) and (2) of the crosslinking method are performed in an enclosed space.

In another preferred embodiment, the steps (1) and (2) of the crosslinking method are performed in a nitrogen or argon atmosphere; preferably, the pressure of the nitrogen atmosphere is 1 atm.

In another preferred embodiment, the surface layer of the ultra-high molecular weight polyethylene substrate is a bearing surface layer of a medical implant.

In another preferred embodiment, the medical implants are partially or wholly made by ultra-high molecular weight polyethylene substrate.

In another preferred embodiment, the ultra-high molecular weight polyethylene substrate is uncrosslinked ultra-high molecular weight polyethylene.

In another preferred embodiment, the medical implants are preformed.

In another preferred embodiment, medical implants are medical implants for plastic surgery.

In another preferred embodiment, the ultra-high molecular weight polyethylene substrate contains antioxidant.

In another preferred embodiment, the antioxidant is one or more selected from the following group: Vitamin E, TTetrakis[methylene(3,5-di-tert-butylhydroxyhydrocinnamate)]methane, Thiodiethylene bis[3-[3,5-di-tert-butyl-4-hydroxyphenyl]propionate], Octadecyl 3,5-di-tert-butyl-4-hydroxylhydrocinnamate, N,N'-hexane-1,6-diylbis(3-(3,5-di-tert-butyl-4-hydroxyphenylpropionamide)), Benzenepropanoic acid, 3,5-bis(1,1-dimethyl-ethyl)-4-hydroxy-.C7-C9 branched alkyl esters, 1,3,5-TRis(3,5-di-tert-butyl-4-hydroxybenzyl)-2,4,6-trimethylbenzene, 2,4-bis (dodecylthiomethyl)-6-methylphenol, Triethylene glycol bis (3-tert-butyl-4-hydroxy-5-methylphenyl)propionate, 2,2'-methylenebis(4-methyl-6-tert-butylphenol)monoacrylate, 1,3,5-TRis(3,5-di-tert-butyl-4-hydroxybenzyl)-1,3,5-triazine-2,4,6(1H,3H,5H)-trione, Benzenamine,N-phenyl-, reaction products with 2,4,4-trimethylpentene, 2,4-bis(octylthio)-6-(4-hydroxy-3,5-di-tert-butylanilino)-1,3,5-triazine, 5,7-di-t-butyl-3-(3,4 di-methylphenyl)-3H-benzofuran-2-one, Tris(2,4-di-tert-butylphenyl)phospite and Pentaerythritol tetra [3-(3,5-di-tert-butyl-4-hydroxyphenyl) propionate].

In another preferred embodiment, the antioxidant is Vitamin E.

In another preferred embodiment, the content of the antioxidant is 0.01-0.20% by weight.

In another preferred embodiment, the content of the antioxidant is 0.01-0.1% by weight.

In another preferred embodiment, the content of the antioxidant is 0.1% by weight.

In another preferred embodiment, the photoinitiator is one or more selected from the following group: benzophenone, 4-chlorobenzophenone, 2-chlorobenzophenone, 4,4'dichlorobenzophenone, 2-methylanthraquinone, 2-ethylanthraquinone, 2-chloroanthraquinone, p-chloro Anthraquinone, benzyl sulfide, benzyl sulfoxide, phenyl sulfoxide, 4-acetylbiphenyl, anthrone, and hexachlorobenzene.

In another preferred embodiment, the photoinitiator is benzophenone.

In another preferred embodiment, in step (1), the diffusion temperature is 50° C.-134° C.

In another preferred embodiment, in step (1), the diffusion temperature is 50° C.-130° C.

In another preferred embodiment, in step (1), the diffusion temperature is 81° C.-130° C.

In another preferred embodiment, in step (1), the diffusion temperature is 90° C.-130° C.

In another preferred embodiment, in step (1), the diffusion period is less than 24 hours (For example 0.1-24 hours).

In another preferred embodiment, in step (1), the diffusion period is less than 12 hours (For example 0.1-12 hours).

In another preferred embodiment, in step (1), the diffusion period is less than 8 hours (For example 0.1-8 hours).

In another preferred embodiment, in step (1), the diffusion period is 0.5-8 hours.

In another preferred embodiment, in step (1), the diffusion period is 1-4 hours.

In another preferred embodiment, the depth that the photoinitiator diffuses into the surface layer of the ultra-high molecular weight polyethylene substrate is 3.5 mm.

In another preferred embodiment, the depth of the photoinitiator diffused into the surface layer of the ultra-high molecular weight polyethylene substrate can be 1-3 mm, 1-2.5 mm or 1-2 mm.

In another preferred embodiment, in step (1), the method further includes the step of cooling the surface layer with diffused photoinitiator to room temperature after diffusing the photoinitiator into the surface layer of the ultra-high molecular weight polyethylene substrate.

In another preferred embodiment, in step (2), the intensity of ultraviolet radiation $\geq 90$ mW/cm$^2$.

In another preferred embodiment, in step (2), the intensity of ultraviolet radiation $\geq 100$ mW/cm2.

In another preferred embodiment, in step (2), the intensity of ultraviolet radiation $\geq 150$ mW/cm$^2$.

In another preferred embodiment, in step (2), the intensity of ultraviolet radiation $\geq 170$ mW/cm$^2$.

In another preferred embodiment, in step (2), the intensity of ultraviolet radiation is 90-250 mW/cm$^2$ or 90-200 mW/cm$^2$.

In another preferred embodiment, in step (2), the intensity of ultraviolet radiation is 100-250 mW/cm$^2$ or 100-200 mW/cm$^2$.

In another preferred embodiment, in step (2), the intensity of ultraviolet radiation is 150-250 mW/cm$^2$ or 150-200 mW/cm$^2$.

In another preferred embodiment, in step (2), the intensity of ultraviolet radiation is 170-250 mW/cm$^2$ or 170-200 mW/cm$^2$.

In another preferred embodiment, in step (2), the period of ultraviolet radiation should be controlled to be $\geq 20$ minutes (for example, 20-200 minutes or 20-100 minutes).

In another preferred embodiment, in step (2), the period of ultraviolet radiation should be controlled to be $\geq 40$ minutes (for example, 40-200 minutes or 40-100 minutes).

In another preferred embodiment, in step (2), the period of ultraviolet radiation should be controlled to be $\geq 60$ minutes (for example, 60-200 minutes or 60-100 minutes).

In another preferred embodiment, in step (2), the depth of ultraviolet light irradiation reaches 3.5 mm.

In another preferred embodiment, in step (2), the depth of ultraviolet light irradiation is 1-3 mm, 1-2.5 mm, 1-2 mm or 1-1.5 mm.

In another preferred embodiment, in step (2), after the crosslinking of the surface layer, a cleaning step is further included: immersing the surface of the gradient cross-linked ultra-high molecular weight polyethylene in an organic solvent; after immersing is finished, drying the surface to obtain a cleaned surface layer gradient crosslinked ultra-high molecular weight polyethylene.

In another preferred embodiment, in step (2), after the cleaning step, a sterilization step is further included: disinfecting the cleaned surface layer gradient crosslinked ultra-high molecular weight polyethylene surface; disinfection is any one of γ-ray sterilization, ETO sterilization, or gas plasma sterilization.

In another preferred embodiment, the total depth of the surface layer gradient crosslinking reaches 3.5 mm.

In another preferred embodiment, the total depth of the surface layer gradient crosslinking reaches 3 mm.

In another preferred embodiment, the total depth of the surface layer gradient crosslinking reaches 2.5 mm.

In another preferred embodiment, in the gradient crosslinking, the depth of super crosslinking reaches 1.5 mm.

In another preferred embodiment, in the gradient crosslinking, the depth of super crosslinking reaches 1.1 mm.

In another preferred embodiment, the diffusion amount of the photoinitiator in the surface layer of the ultra-high molecular weight polyethylene substrate is greater than 0.9 mg/cm$^2$.

In another preferred embodiment, the diffusion amount of the photoinitiator in the surface layer of the ultra-high molecular weight polyethylene substrate is greater than 1.11 mg/cm$^2$.

In another preferred embodiment, the diffusion amount of the photoinitiator in the surface layer of the ultra-high molecular weight polyethylene substrate is 0.9-10 mg/cm$^2$.

In another preferred embodiment, the diffusion amount of the photoinitiator in the surface layer of the ultra-high molecular weight polyethylene substrate is 1-8 mg/cm$^2$.

The second aspect of the present invention provides an ultra-high molecular weight polyethylene medical implant, the medical implant are partly or entirely made of ultra-high molecular weight polyethylene, the medical implant has at least one bearing surface layer made of ultra-high molecular weight polyethylene, the bearing surface layer is gradient crosslinked, the bearing surface layer is super crosslinked, highly crosslinked and low-degree crosslinked in order from the surface to the inside.

In another preferred embodiment, the total depth of gradient crosslinking reaches 3.5 mm.

In another preferred embodiment, the total depth of gradient crosslinking reaches 3 mm.

In another preferred embodiment, the total depth of gradient crosslinking reaches 2.5 mm.

In another preferred embodiment, in the gradient crosslinking, the depth of super crosslinking reaches 1.5 mm.

In another preferred embodiment, in the gradient crosslinking, the depth of super crosslinking reaches 1 mm.

In another preferred embodiment, the ultra-high molecular weight polyethylene includes antioxidant.

In another preferred embodiment, the antioxidant is one or more selected from the following group: Vitamin E, Tetrakis[methylene(3,5-di-tert-butylhydroxyhydrocinnamate)]methane, Thiodiethylene bis[3-[3,5-di-tert-butyl-4-hydroxyphenyl]propionate], Octadecyl 3,5-di-tert-butyl-4-hydroxylhydrocinnamate, N,N'-hexane-1,6-diylbis(3-(3,5-di-tert-butyl-4-hydroxyphenylpropionamide)), Benzenepropanoic acid, 3,5-bis(1,1-dimethyl-ethyl)-4-hydroxy-.C7-C9 branched alkyl esters, 1,3,5-TRis(3,5-di-tert-butyl-4-hydroxybenzyl)-2,4,6-trimethylbenzene, 2,4-bis(dodecylthiomethyl)-6-methylphenol, Triethylene glycol bis (3-tert-butyl-4-hydroxy-5-methylphenyl)propionate, 2,2'-methylenebis(4-methyl-6-tert-butylphenol)monoacrylate, 1,3,5-TRis(3,5-di-tert-butyl-4-hydroxybenzyl)-1,3,5-triazine-2,4,6(1H,3H,5H)-trione, Benzenamine,N-phenyl-, reaction products with 2,4,4-trimethylpentene, 2,4-bis(octylthio)-6-(4-hydroxy-3,5-di-tert-butylanilino)-1,3,5-triazine, 5,7-di-t-butyl-3-(3,4 di-methylphenyl)-3H-benzofuran-2-one, Tris(2,4-di-tert-butylphenyl)phospite and pentaerythritol tetra [3-(3,5-di-tert-butyl-4-hydroxyphenyl) propionate].

In another preferred embodiment, the antioxidant is Vitamin E.

In another preferred embodiment, the content of antioxidant is 0.01-0.20% by weight.

In another preferred embodiment, the content of antioxidant is 0.01-0.1% by weight.

In another preferred embodiment, the content of antioxidant is 0.1% by weight.

In another preferred embodiment, the bearing surface layer of the medical implant is crosslinked by the crosslinking method described in the first aspect of the present invention.

In another preferred embodiment, the average fracture force of the 0.25 mm thick film of the outermost surface layer of bearing surface layer is greater than 50.0 Newtons.

In another preferred embodiment, the equivalent crosslinking degree of the outermost surface layer of the bearing surface layer is more than 100 kGy.

The third aspect of the present invention provides a medical joint comprising a first joint bearing body and a second joint bearing body, wherein an ultra-high molecular weight polyethylene medical implant according to the second aspect of the present invention is provided between the first joint bearing body and the second joint bearing body.

In another preferred embodiment, the medical joint can be any artificial joint, such as an artificial hip joint, an artificial shoulder joint, an artificial knee joint, an artificial condyle joint, an artificial elbow joint, an artificial wrist joint, an artificial finger joint, and the like.

In another preferred embodiment, if the medical joint is a hip joint, the first joint bearing body is an acetabular cup, and the second joint bearing body is a femoral head.

It should be understood that, within the scope of the present invention, the above technical features of the present invention and the technical features specifically described in the following (eg, embodiments) can be combined with each other, thereby forming new or preferred technical solutions. For brief, such solutions will not be described one by one.

Advantages of the Invention

The US Food and Drug Administration (FDA) classified artificial joint materials made of ultra-high molecular weight polyethylene (UHMWPE) into four categories. The first category is traditional ultra-high molecular weight polyethylene with a crosslinking degree of less than 40 kGy, which has been invented and put into clinical practice since 1960. The second category is highly crosslinked ultra-high molecular weight polyethylene with a crosslinking degree of 50-100 kGy, which was invented and put into clinical practice since the 1990's. The third category is highly crosslinked ultra-high molecular weight polyethylene containing antioxidant with a crosslinking degree of 100 kGy, which has been invented and put into clinical practice since 2005. The fourth category of materials are the others, such as surface crosslinked ultra-high molecular weight polyethylene, which has been invented since 2000 but has not been put into clinical practice. The surface crosslinked ultrahigh molecular weight polyethylene obtained by the present invention is a surface gradient crosslinked ultrahigh molecular weight polyethylene, and the crosslinking degree and chemical composition cover the first three categories of materials and belong to the fourth category.

The surface gradient crosslinked ultra-high molecular weight polyethylene obtained by the process of the present invention breaks through the technical limits of the first three categories of polyethylene and can expand its application range.

The surface gradient crosslinked ultra-high molecular weight polyethylene of the present invention has super wear resistance, it can completely replace ceramics, so that brittle fracture of ceramics will become past history. The sensitivity caused by metal ions to patients and the toxicity of wear debris can be radically eliminated by replacing the metal with the surface gradient crosslinked ultra-high molecular weight polyethylene of the present invention. The manufactured artificial joint no longer needs metal for a mechanical bearing, because the surface gradient crosslinked ultra-high molecular weight polyethylene of the present invention is not only crosslinked in bulk, but also can reduce at least 50% of the manufacturing cost of metal or ceramics. Moreover, components can be made quite thin with the surface gradient crosslinked ultra-high molecular weight polyethylene of the present invention, which minimizes bone cut during surgery. Wear resistance and toughness of the artificial joints made from bulk crosslinked ultra-high molecular weight polyethylene are uncompromisable, so doctors advise patients with joints not to do strenuous exercise such as running, jumping or climbing. In contrast, patients using artificial joints made of the surface gradient cross-linked ultra-high molecular weight polyethylene of the present invention are not so limited.

The process of the present invention has the following improvements:

Firstly, the step of the γ-rays pre-crosslinking in the prior art is eliminated.

Secondly, the photoinitiator is diffused to the polyethylene surface to a depth greater than 1.0 mm by high-temperature gas-phase diffusion at a temperature above the melting point of the photoinitiator.

Third, high-intensity ultraviolet light irradiation (>100 mW/cm$^2$) is used to ensure that the deep-diffused photoinitiator is completely crosslinked with the ultra-high molecular weight polyethylene.

It has achieved significant technical effects through process improvements in the above four aspects:

One, it will not cut the main chain of polyethylene molecule because of without γ-rays pre-crosslinking, which overcome the shortcomings that the bulk becomes brittle. As the degree of crosslinking increases, the two-dimensional tensile fracture toughness of the surface gradient crosslinked ultrahigh molecular weight polyethylene of the present invention also increases as well.

This is unexpectedly contrary to the data disclosed in the prior art (see FIG. 1, FIG. 2, FIG. 3, and FIG. 6).

Two, the surface gradient crosslinked ultra-high molecular weight polyethylene of the present invention exhibits super crosslinking, the crosslinking degree can be increased to 250 kGy or more, and the thickness of super crosslinking exceeds 1.0 mm.

Three, the total crosslinking depth of the surface gradient crosslinked ultra-high molecular weight polyethylene of the present invention exceeds 1.0 mm.

Four, the super wear resistance of the polyethylene surface is retained by introducing a very small amount of antioxidant in the surface layer of polyethylene (<0.1 wt %), there is no need to remove the surface layer since the surface is not oxidized. It still has a lower wear rate than 100 kGy highly crosslinked ultra-high molecular weight polyethylene in the case where the surface of the cobalt-chromium alloy ball is rough.

EMBODIMENTS

Figure 1:
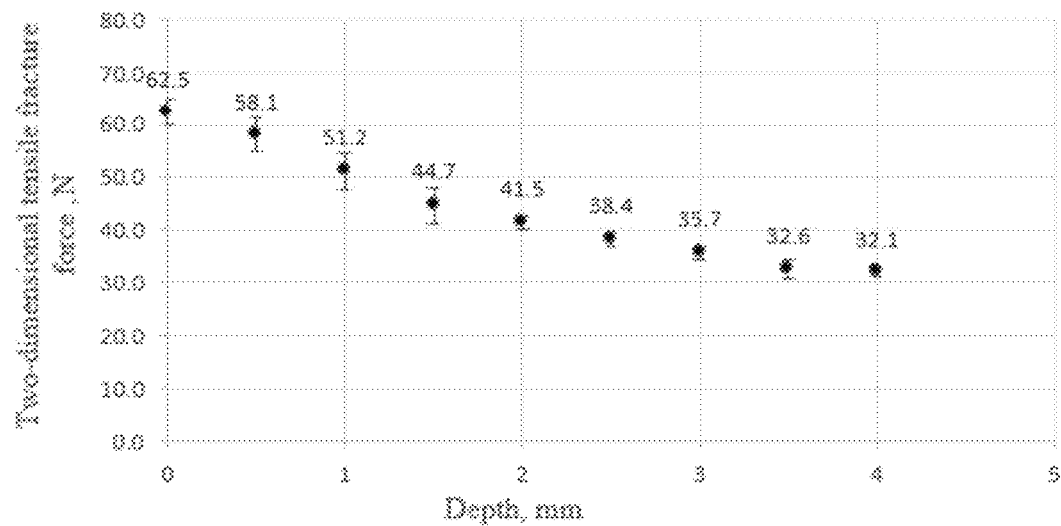
FIG. 1 shows ultimate load relation to crosslinking depth of 0.25 mm films tested by small punch. The test samples were machined from surface super crosslinked ultra-high molecular weight polyethylene GUR1020 E (0.1 wt % viE) made by Embodiment 8.

Hereinafter, preferred embodiments of the present application will be described in detail with reference to the drawings, so as to more clearly understand the objects, features, and advantages of the present application. It should be understood that the embodiments shown in the drawings are not intended to limit the scope of the present application, but merely to explain the essential spirit of the technical solution of the present application.

In the following description, certain specific details are set forth for the purpose of illustrating various disclosed embodiments to provide a thorough understanding of the various embodiments. One skilled in the art will recognize, however, that the embodiments may be realized without one or more of these specific details. In other cases, well-known devices, structures, and techniques associated with the present application may not be shown or described in detail to avoid unnecessarily obscuring the description of the embodiments.

The words "including" and variations such as "comprising" and "having" in the specification and claims should be construed as open and inclusive meaning that they should be construed as "including, but not limited to", unless the context requires otherwise.

Reference throughout the specification to "one embodiment" or "an embodiment" means that a particular feature, structure, or characteristic described in connection with the embodiment is included in at least one embodiment. Thus, expression of "in one embodiment" or "In one embodiment" in various places throughout the specification are not necessarily all referring to the same embodiment. Furthermore, the particular features, structures, or characteristics may be combined in any manner in one or more embodiments.

As used in this specification and the appended claims, the singular forms "a", "the" and "said" include plural referents unless the context clearly dictates otherwise. It should be noted that the term "or" is generally used in its sense including "and/or" unless the context clearly dictates otherwise.

In the context, the "surface gradient crosslinked ultra-high molecular weight polyethylene" obtained by the process of the present invention may also be referred to as "surface super crosslinked ultra-high molecular weight polyethylene" in the present invention.

Two-dimensional tensile fracture force of film: refers to the highest fracture force or final fracture force of two-dimensional tensile of a 0.25 mm thick film conforming with the ASTM F2977-13 standard.

Two-dimensional tensile fracture toughness of film: refers to the work to be done by two-dimensional tensile a 0.25 mm thick film conforming with ASTM F2977-13 standard until breaking.

Equivalent crosslinking degree: the two crosslinking methods have the same crosslinking degree if they achieve the same two-dimensional tensile fracture force. The equivalent crosslinking degree can theoretically also be obtained by measuring the crosslink density or the Trans-vinylene index. The unit of equivalent crosslinking degree is kGy.

Figure 9:
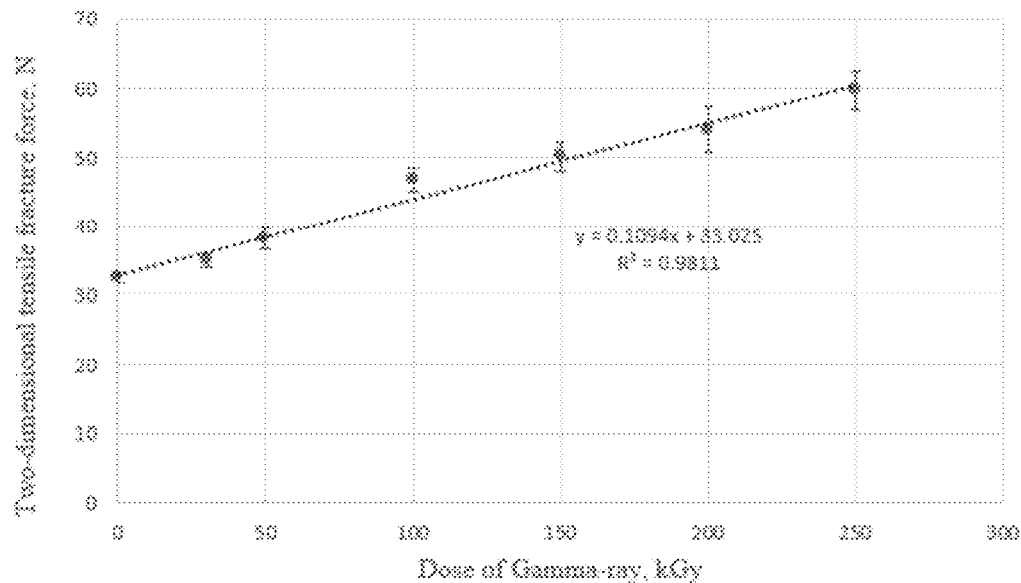
FIG. 9 shows the linear relationship between ultimate load and crosslinking dose of γ-ray irradiation of the ultra-high molecular weight polyethylene GUR1020E (0.1% VitE). The test film thickness is 0.25 mm.
Figure 10:
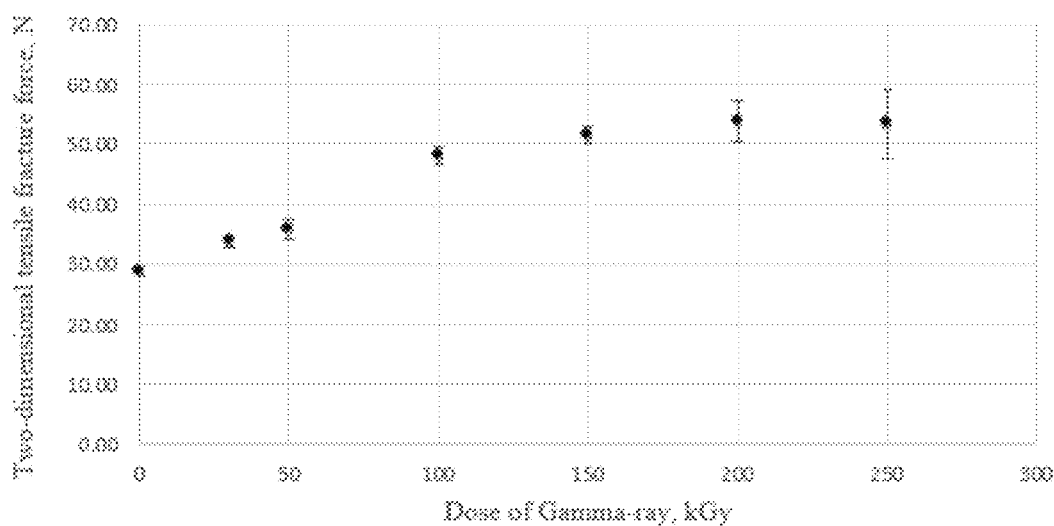
FIG. 10 shows the relationship between ultimate load and crosslinking dose of γ-ray irradiation of the ultra-high molecular weight polyethylene GUR1020. The film thickness is 0.25 mm film.

So far, the test methods used for bulk are not suitable for gradient crosslinking. Being inspired by the mathematical differential method, the invention adopts the film test method of Reference 15, takes a 0.25 mm film in the gradient layer, and performs layer-by-layer two-dimensional tensile mechanical testing in accordance with the ASTMF2183 standard. Radiation crosslinking correction is performed on the two-dimensional tensile data to obtain an equivalent crosslinking degree. The two-dimensional tensile fracture force of the ultra-high molecular weight polyethylene GUR1020E containing 0.1% by weight of vitamin E is linearly related to the dose of gamma rays in the range of 0-250 kGy (FIG. 9). However, for the ultra-high molecular weight polyethylene GUR1020 without vitamin E, the linear relationship does not exist in the range of 100-250 kGy (FIG. 10).

In the present invention, $\gamma$-ray crosslinking is selected as the calibration method, and ultraviolet-assisted photoinitiator surface crosslinking is calibrated. For example, for an ultra-high molecular weight polyethylene GUR1020E containing 0.1% by weight of vitamin E, the equivalent crosslinking degree is obtained from the calibration straight line formula shown in FIG. 9:

$$\text{Equivalent crosslinking degree} = (\text{two-dimensional tensile fracture force of film} - 33.02)/0.109$$

Super crosslinking: the equivalent crosslinking degree is greater than 100 kGy dose of $\gamma$-rays. The 100 kGy is corresponding to 50 Newtons of the two-dimensional tensile fracture force of 0.25 mm thick ultra-high molecular weight polyethylene film.

Highly crosslinking: The equivalent crosslinking degree is 50-100 kGy dose of $\gamma$-rays. The 50-100 kGy is corresponding to 38.5-50 Newtons of the two-dimensional tensile fracture force of 0.25 mm thick ultra-high molecular weight polyethylene film.

Low-degree crosslinking: The equivalent crosslinking degree is 30-50 kGy dose of $\gamma$-rays. 30-50 kGy is corresponding to 36.5-38.5 Newtons of the two-dimensional tensile fracture force of 0.25 mm thick ultra-high molecular weight polyethylene film.

Non-crosslinking: Gamma rays with an equivalent crosslinking degree of less than 30 kGy, which is corresponding to less than 36 Newtons of a 0.25 mm thick ultra-high molecular weight polyethylene film have a two-dimensional tensile breaking force.

Cross-linking depth: The distance from one level of crosslinking to another.

Total depth of gradient crosslinking: the distance by which the surface super crosslinking gradually decays to non-crosslinking in the body, that is, the sum of the depth or thickness of the super crosslinking, high crosslinking and low crosslinking.

Various aspects of the invention are described in detail below.

Substrate

The substrate used in the present invention can be an uncrosslinked ultra-high molecular weight polyethylene produced by compression molding or ram-extrusion molding of resins by Ticona or other companies (for example, GUR1020 or GUR1050). The substrate used in the present invention may or may not contain antioxidants. The optional antioxidants can be any one or more selected from the following groups: Vitamin E, Irganox®1010, Irganox®1035, Irganox®1076, Irganox®1098, Irganox®1135, Irganox® 1130, Irganox®1520, Irganox®1726, Irganox®245, Irganox®3052, Irganox® 3114, Irganox®5057, Irganox®565, Irganox® HP-136, Ingafos®168, orpentaerythritol tetrakis[3-(3,5-di-tert-butyl-4-hydroxyphenyl) propionate, see Table 1. The content of antioxidant is 0.05-0.20% by weight, for example, preferably 0.1% by weight.

The substrate used in the present invention may preferably use uncrosslinked ultra-high molecular weight polyethylene containing 0.1% by weight of vitamin E, which can be referred as uncrosslinked ultra-high molecular weight polyethylene (0.1 wt % vitamin E) or uncrosslinked ultrahigh molecular weight polyethylene (0.1 wt % ViE). For example, the uncrosslinked ultra-high molecular weight polyethylene GUR1020 containing 0.1% by weight of vitamin E may be abbreviated as ultra-high molecular weight polyethylene GUR1020E or directly abbreviated as GUR1020E.

TABLE 1

Chemical names and structures of some antioxidants trademarked under the Irganox ® name

| Tradename | Chemical name | Chemical Structure |
|---|---|---|
| Irganox ® 1010 | Tetrakis[methylene(3,5-di-tert-butyl-hydroxyhydrocinnamate)methane | 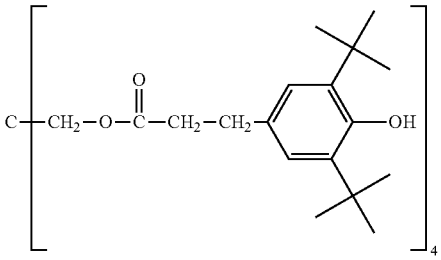 1178 g/mol |
| Irganox ® 1035 | Thiodiebylene bis [3-[3,5-di-tert-butyl-4-hydroxyphenyl]propionate] | 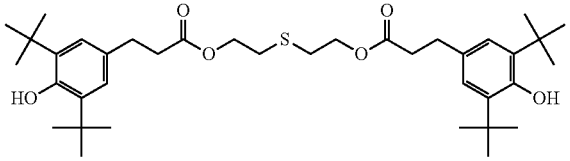 [SMILES: CC(C)(C)c1cc(CCC(=O)OCCSCCOC(=O)CCc2cc(C(C)(C)C)c(O)c(C(C)(C)C)c2)cc(C(C)(C)C)c1O] |
| Irganox ® 1076 | Octadecyl 3,5-di-tert-butyl-4-hydroxyl-hydrocinnimate | 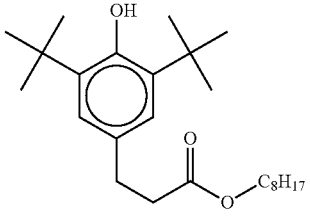 |
| Irganox ® 1098 | N,N'-hexane-1,6-diylbis(3-(3,5-di-tert-butyl-1-4-hydroxyphenylpropionamide)) | 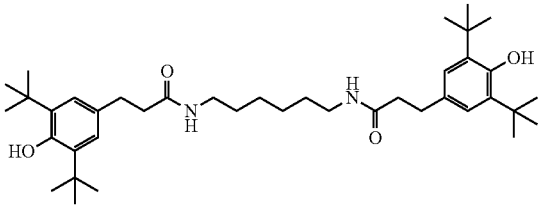 [SMILES: CC(C)(C)c1cc(CCC(=O)NCCCCCCNC(=O)CCc2cc(C(C)(C)C)c(O)c(C(C)(C)C)c2)cc(C(C)(C)C)c1O] |
| Irganox ® 1135 | Benzenepropanoic acid, 3,5-bis(1,1-dimethyl-ethyl)-4-hydroxy-C7-C9 branched alkyl esters | 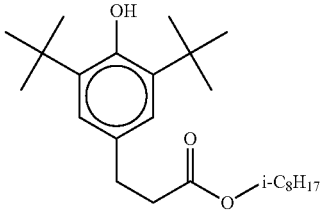 390 g/mol |

TABLE 1-continued

Chemical names and structures of some autioxidants trademarked under the Irganox ® name

| Tradename | Chemical name | Chemical Structure |
|---|---|---|
| Irganox ® 1330 | 1,3,5-TRis(3,5-di-tert-butyl-4-hydroxybenzyl)-2,4,6-trimethylbenzene | 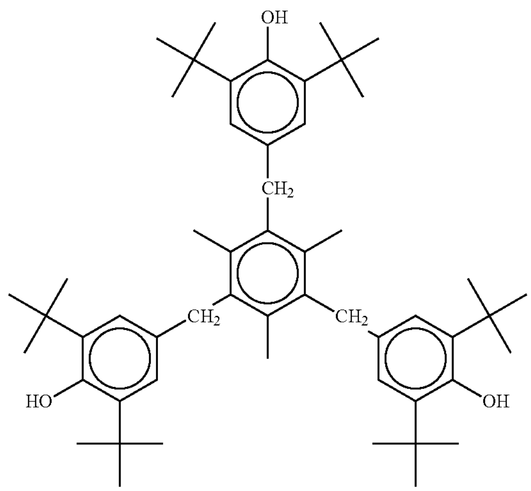 |
| Irganox ® 1520 | | 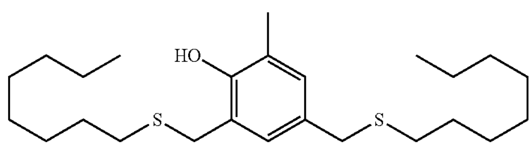 [SMILES: CCCCCCCCSCc1cc(C)c(O)c(CSCCCCCCCC)c1] |
| Irganox ® 1726 | 2,4-bis(dodecylithiomethyl)-6-methylphenol | 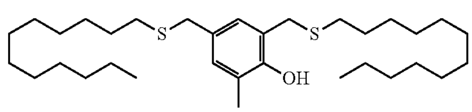 [SMILES: CCCCCCCCCCCCSCc1cc(C)c(O)c(CSCCCCCCCCCCCC)c1] |
| Irganox ® 245 | Triethylene glycol bis(3-tert-butyl-4-hydroxy-5-methylphenyl)propionate | 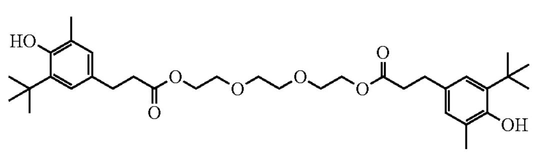 [SMILES: Cc1cc(CCC(=O)OCCOCCOCCOC(=O)CCc2cc(C)c(O)c(C(C)(C)C)c2)cc(C(C)(C)C)c1O] |
| Irganox ® 3052 | 2,2'-methylenebis(4-methyl-6-tert-butylphenol)monoacrylate | 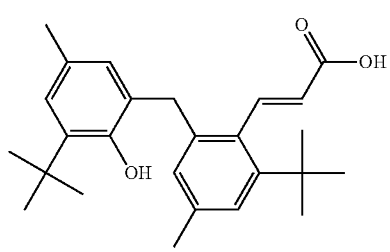 [SMILES: Cc1cc(Cc2cc(C)cc(C(C)(C)C)c2/C=C/C(=O)O)c(O)c(C(C)(C)C)c1] |

TABLE 1-continued

Chemical names and structures of some autioxidants trademarked under the Irganox ® name

| Tradename | Chemical name | Chemical Structure |
| --- | --- | --- |
| Irganox ® 3114 | 1,3,5-TRis(3,5-di-tert-butyl-4-hydroxy benzyl)-1,3,5-triazine-2,4,6(1H,3H,5H)-trione | 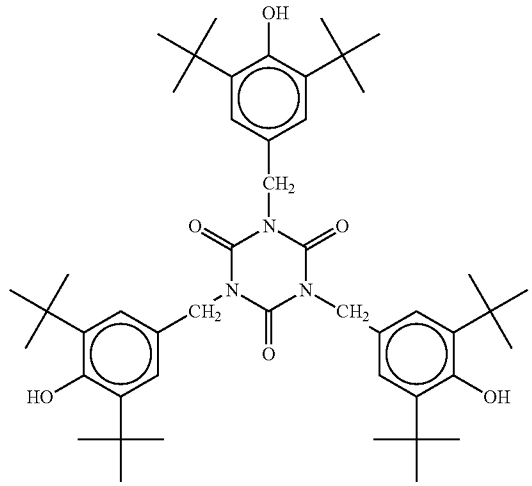 |
| Irganox ® 5057 | Benzenamine,N-phenyl-,reaction products with 2,4,4-trimethylpentene | R, R$_1$ = H, C$_4$H$_9$, or C$_8$H$_{17}$ and other alkyl chains |
| Irganox ® 565 | 2,4-bis(octylthio)-6-(4-hydroxy-3,5-di-tert-butylamilino)-1,3,5-triazine | 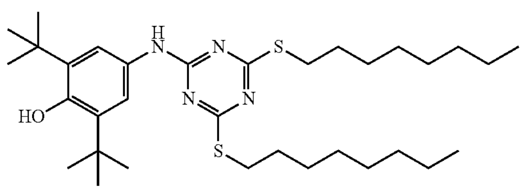 [SMILES: CCCCCCCCSc1nc(Nc2cc(C(C)(C)C)c(O)c(C(C)(C)C)c2)nc(SCCCCCCCC)n1] |
| Irganox ® HP-136 | 5,7-di-t-butyl-3-(3,4-di-methylphenyl)-3H-benzofuran-2-one | 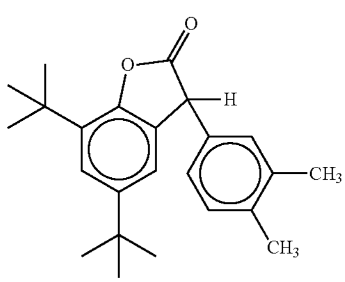 |
| Ingafox ® 168 | Tris(2,4-di-tert-butylphenyl)phospite | 646.9 g/mol |

The substrate of the present invention can be processed through a surface diffusion process and a surface crosslinking process. Preferably, a surface cleaning process and a surface sterilization process can further be performed after the surface crosslinking process.

Before the surface diffusion process, the substrate of the present invention can also be subjected to preliminary processing and further processing of the substrate so that the substrate is firstly machined into a component, for example, a medical implant. The medical implant in the present invention refers to a component that can be implanted into a body (such as a human body). In another preferred example, the medical implant is used as a wear-resistant device in artificial joints (such as hip joints, shoulder joints, knee joints, and etc.).

The following describes the steps of the surface gradient cross-linking method of the present application.

Preliminary Processing (Consolidation)

The substrate of the present invention can be preliminarily processed into various forms (for example, rectangular plates or bars, etc.) of ultra-high molecular weight polyethylene materials by molding or extruding. The manufacturers that can be used in this step include: British Orthoplastic, Ltd, American MediTech Inc, and American Restoration Medical Polymer, Inc.

Further Processing

The ultra-high molecular weight polyethylene material (for example, rectangular plates or bars) obtained by preliminary processing can be further processed into various forms of ultra-high molecular weight polyethylene parts by mechanical processing, for example, small plates or artificial joints. The resulting parts can be subjected to the following series of processes. Acetone and other solvents can be used to clean the surface of the components to remove impurities on the surface before proceeding to the following process.

Surface Diffusion Process

The photoinitiator is diffused into the wear surface of the processed ultra-high molecular weight polyethylene components (for example, small flat plates or artificial joints). The optional photoinitiator of the present invention can be one or more selected from the following group: benzophenone, 4-chlorobenzophenone, 2-chlorobenzophenone, 4,4'dichlorobenzophenone, 2-methylanthraquinone, 2-ethylanthraquinone, 2-chloroanthraquinone, p-chloro anthraquinone, benzyl sulfide, benzyl sulfoxide, phenyl sulfoxide, 4-acetylbiphenyl, anthrone, and hexachlorobenzene. Benzophenone is preferable.

Benzophenone is taken as an example of the photoinitiator, the surface diffusion process of benzophenone can include the following steps: placing ultra-high molecular weight polyethylene components (for example, ultra-high molecular weight polyethylene GUR1020E small plate or artificial joint) on an aluminum plate; then placing the aluminum plate in a stainless steel container for diffusion. The stainless steel container contains solid benzophenone powder. The container has a ventilated pipe through the sidewall thereof which is connected to the mechanical pump for evacuating the container. After evacuating the container, nitrogen was passed in, the above process is repeated three times, during which the container is kept sealed and the nitrogen pressure is about one atmosphere. The entire stainless steel container is putting into a low-temperature oven, the photoinitiator benzophenone and UHMWPE components are heated to a certain temperature at the same time, and the photoinitiator benzophenone is diffusing on the surface of UHMWPE for a period. The ultra high molecular weight polyethylene components are cooled to room temperature after the surface of the ultra-high molecular weight polyethylene is diffused in by the photoinitiator.

The diffusion temperature is controlled to be 50° C.-134° C., the minimum diffusion temperature should exceed the melting point of benzophenone by about 49° C. to keep the benzophenone in a liquid state. Liquid benzophenone has a relatively high saturate vapor pressure. By increasing the diffusion temperature, it is beneficial to the rapid diffusion of benzophenone gas into ultra-high molecular weight polyethylene, shortening process time. Since the ultra-high molecular weight polyethylene will deform at the temperature higher than 134° C., the maximum diffusion temperature should be lower than about 134° C., the melting point of ultra-high molecular weight polyethylene. The preferred diffusion temperature is between 50° C. and 30° C., more preferably between 80° C. and 130° C., and most preferably between 90° C. and 130° C. The diffusion period is controlled to be less than 24 hours, more preferably less than 12 hours, and most preferably less than 8 hours. The diffusion temperature and period should be adjusted accordingly for large-sized components and large-scale production.

Surface Crosslinking Process

The ultra-high molecular weight polyethylene components (for example, ultra-high molecular weight polyethylene GUR1020E small plate or artificial joint) thereon is put on aluminum plate in a the stainless steel container. The pipeline passing through the sidewall of the container is connected to a mechanical pump for evacuating the container. After evacuating the container, nitrogen was passed in, and the above process is repeated three times, during which the container is kept sealed and the nitrogen pressure is about one atmosphere. The container has a transparent glass lid on the top. Crosslinking is performed by shining ultraviolet light though glass lid on the surface of UHMWPE.

The ultraviolet light can be that of any brand in the market. The average wavelength of ultraviolet radiation is 320-390 nanometers; preferably 365 nanometers. The radiation intensity of the ultraviolet light is controlled by adjusting the power and radiation distance of the ultraviolet light. The radiation intensity of the ultraviolet light on the surface of the ultra high molecular weight polyethylene should be controlled to be ≥90 mW/cm$^2$, preferably ≥100 mW/cm$^2$, more preferably ≥150 m W/cm$^2$, and most preferably ≥170 mW/cm$^2$. The radiation period of ultraviolet light should be controlled to be ≥20 minutes, preferably ≥40 minutes, and most preferably ≥60 minutes.

The ultra-high molecular weight polyethylene (such as ultra-high molecular weight polyethylene GUR1020E) materials or components are machined into a variety of circular sheet.

Figure 11:
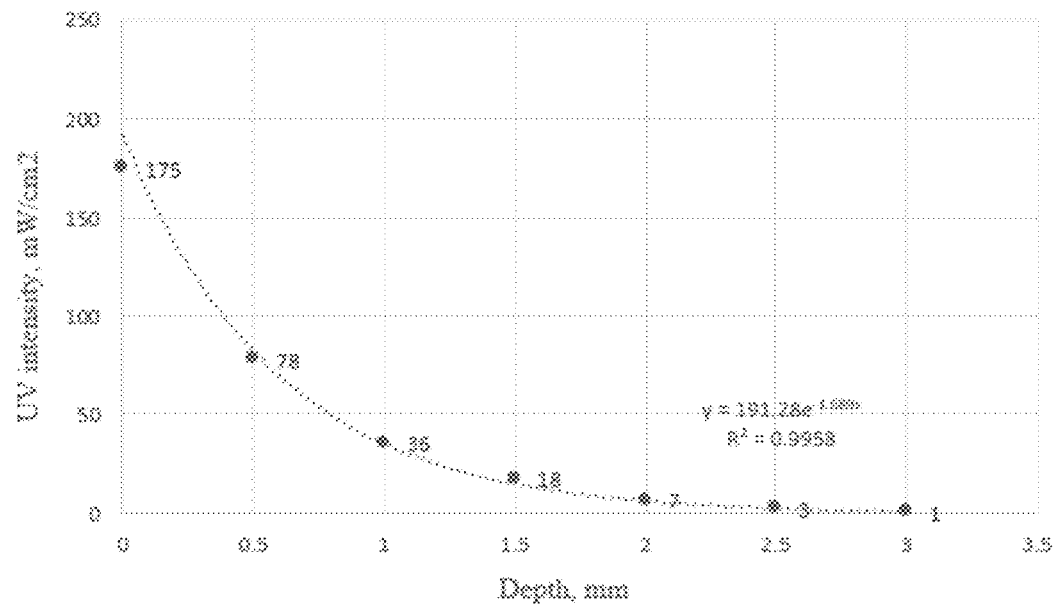
FIG. 11 shows the ultraviolet light radiation intensity change with the depth of ultra-high molecular weight polyethylene GUR1020 E (0.1% wt ViE) in the crosslinking process of the present invention.

The diameter of the circular sheet is 25.4 mm; the thickness of the circular sheet is 0.5 mm, 1.0 mm, 1.5 mm, 2 mm, 2.5 mm, and 3 mm, respectively. The sheets are stacked and an ultraviolet intensity tester is placed below the sheets, The curve of the variation of ultraviolet light intensity with the thickness of the sheet was tested. Taking ultra-high molecular weight polyethylene GUR1020E as an example, the results are shown in FIG. 11: the intensity of ultraviolet light decays as the thickness of the slice increases. Therefore, providing a sufficiently high ultraviolet light intensity is one of the necessary conditions for increasing the depth of crosslinking of the surface layer.

When radiating the ultraviolet light, the surface color of the ultra-high molecular weight polyethylene diffused by the photoinitiator of benzophenone gradually changed from dark yellow to light white. There is no color change on the surface of ultra high molecular weight polyethylene undiffused by photoinitiator of benzophenone. It was proved by the facts that the photoinitiator of benzophenone, under the action of ultraviolet light, participated in the surface cross-linking of ultra-high molecular weight polyethylene. And, the color tends to be stable as crosslinking progresses proceeded over time, indicating that benzophenone is gradually being depleted. Where the surface is not diffused by the photoinitiator, there is no color change on the surface of ultra-high molecular weight polyethylene under exposition of ultraviolet light, indicating there is no crosslinking reaction occurs.

Surface Cleaning Process

The component surface is cleaned after the surface of ultra high molecular weight polyethylene component is diffused and crosslinked. The cleaning method includes: immersing the ultra high molecular weight polyethylene component into an organic solvent, so as to remove the unreacted photoinitiator of benzophenone and any soluble by-product such as benzopinacol. The optional organic solvent can be selected from the following group: acetone, ethanol, methanol, isopropanol, ether, etc. The organic solvent is preferably acetone. The UV crosslinked component is placed in a air convection oven for drying of cleaning agent (for example, 70° C. for 1 hour).

Surface Sterilization Process

The surface of the component can be sterilized after cleaning process. Sterilization methods include any one of sterilization with gamma rays, ETO sterilization, and gas plasma sterilization.

After the above process, the obtained surface gradient cross-linked ultra-high molecular weight polyethylene components were tested as follows:

Two-Dimensional Tensile Mechanical Property Testing (Small Punch)

Figure 7:
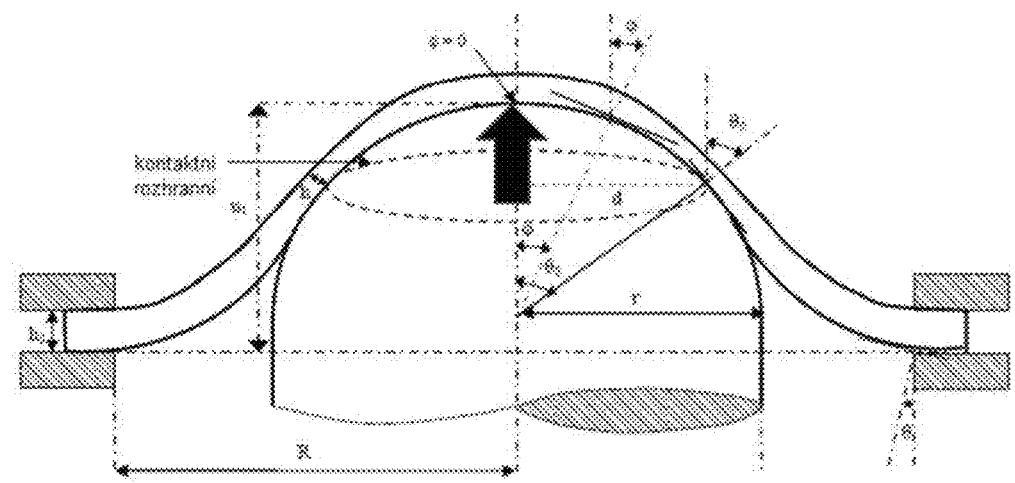
FIG. 7 shows schematic diagram of small punch testing. A 0.25 mm film was fixed in a small hole. A hemisphere metal pin punches to the film until the film breaks. A load vs displacement curve is recorded. The area under the curve is work to failure, i.e., fracture toughness.

The two-dimensional tensile mechanical property testing of the present invention is generally carried out according to the method of ASTM F2977-13 (Reference 7). Two adjustments were made at the same time: First, the thickness of the testing sample is changed from 0.508+0.005/−0.008 mm to 0.250+0.005/−0.008 mm; second, the diameter of the inner hole of the grinding tool is changed from 3.8 mm to 3.4 mm. The thickness of the test sample is reduced to precisely measure the gradient cross-linking, the smaller diameter of the inner hole of the grinding tool is to avoid the sliding test error caused by the thinner sample thickness (Reference 8). For the surface gradient cross-linked ultra-high molecular weight polyethylene sample of the present invention, a cylindrical sample with a diameter of 6.350+0.000/−0.127 mm was taken out of the bulk. From the wear surface, films are obtained layer by layer from the outside to the inside by 0.25 mm (Reference 9). A two-dimensional tensile mechanical test is performed according to the adjusted ASTM F2977-13 method to obtain variation curve of the two-dimensional tensile fracture force of the film with the film stretching length (the schematic drawing of the film stretching method is shown in FIG. 7). Specifically, during testing, the two-dimensional film is clamped in a small hole, and a hemispherical metal needle is pushed on the film until the film breaks, and the curve of the force and elongation of the film is recorded. The final fracture force is the two-dimensional tensile fracture force of the film, and the area under the curve is the two-dimensional tensile fracture toughness of the film. The end point of the curve is the highest fracture force, and the area under the curve is the fracture toughness. Six films selected for each testing point were individually tested, and then the average and standard deviations were calculated.

Equivalent Crosslinking Degree Correction

The ultra-high molecular weight polyethylene GUR1020 and ultra-high molecular weight polyethylene GUR1020E are processed into a film with a diameter of 6.350+0.000/−0.127 mm and a thickness of 0.250+0.005/−0.008 mm, and is enclosed in a gas sealed Mylar aluminum foil bag. Then, the bag is evacuated by a mechanical pump, and nitrogen is passed in, which is repeated three times to maintain the vacuum bag in sealed state, the film therein is crosslinked by γ-ray, and then is annealed at 80° C. The samples obtained through the above steps were tested for two-dimensional tensile mechanical properties. The radiation cross-linking calibration line of ultra-high molecular weight polyethylene GUR1020E was obtained by plotting the γ-ray radiation amount and the final fracture force of the two-dimensional tensile mechanical property test (FIG. 9). The calibration line can be used for the correction of the equivalent cross-linking degree of the surface cross-linking ultra-high molecular weight polyethylene GUR1020E. The result is that the equivalent crosslinking degree follows a linear relationship only within the range of 0-100 kGy for the ultra-high molecular weight polyethylene GUR1020 without vitamin E, when the equivalent crosslinking degree is more than 100 kGy, the tensile fracture force of the two-dimensional film remains basically unchanged, with an average value thereof fluctuating between 50 and 53 Newtons (FIG. 10). Therefore, the equivalent cross-linking degree calibration is not suitable for ultra-high molecular weight polyethylene GUR1020 at more than 100 kGy.

The equivalent crosslinking degree can theoretically be obtained by measuring the crosslink density according to ASTM D2765. The higher the degree of crosslinking, the greater the crosslinking density. Crosslinking density testing is an indirect testing method: dissolving the crosslinked ultra-high molecular weight polyethylene in xylene at 130° C., measuring the weight change before and after dissolution, and calculating the swell ratio. Then, the swell ratio is converted to the crosslink density. The ultra-high molecular weight polyethylene with low to high degree crosslinking absorbs a larger amount of xylene, and the test of crosslink density is more accurate. However, the amount of xylene absorbed by the super crosslinked ultra-high molecular weight polyethylene is extremely low, and the measurement deviation is very large due to being limited by the accuracy of the balance. Therefore, it is not employed by the present invention.

The equivalent cross-linking degree, according to ASTMD2381, can theoretically be obtained by measuring the Trans-vinylene index (referred to as TVI) with Infrared spectrum. The higher the degree of crosslinking, the greater the TVL, TVI, as an indirect test method, measures the ratio of the absorption peak area of 965 cm-1 to the absorption peak area of 965 cm-1 and 1900 cm-1 in the infrared spectrum of ultra-high molecular weight polyethylene. TVI was tested in the present invention, but the deviation was large.

Surface Gradient Cross-Linking Degree Curve:

The basis for testing the degree of crosslinking in the present invention is the calibration as shown in FIG. 9, and the two-dimensional tensile fracture force is proportional to the dose of γ rays. The degree of crosslinking equivalent to equal dose of γ-ray is obtained through the fracture force of the film, which is called the equivalent crosslinking degree. For the ultra-high molecular weight polyethylene samples having super crosslinked surface of the present invention or the super-high molecular weight polyethylene samples with surface cross-linked in the reference, 0.25 mm films from the gradient crosslinking layer on the wear surface of the bearing, test the two-dimensional tensile fracture force depth curve (FIG. 1 and FIG. 4) to obtain the surface cross-linking depth curve (FIG. 2) and the surface toughness depth curve ((FIG. 3 and FIG. 5).

Abrasion Testing

The abrasion test was conducted on the Germany EndoLab®, Hip Joint C6/2-07 Model Wear Test Machine, according to ISO4242-1 standard. The applied force is the Paul curve that simulates human walking. The median angle is 30° (corresponding to clinical 45°), flexion/extension is +25°/−18°, adduction/abduction is −4°/+7°, cycle frequency is 1.0 Hz, maximum force is 3000 Newtons, and the temperature is 37.0±2.0° C. Four samples were selected as a test group and four samples were selected as the comparison group in the testing. Three samples in each group are used for abrasion test, and one sample is used for water loss and water absorption correction.

The test group samples are the super-high molecular weight polyethylene with super-crosslinked surface of the invention, a concave-hemispherical hip joint with a diameter of 44.2 mm and a surface-roughened cobalt-chromium alloy convex-hemispherical hip joint with a diameter of 44.0 mm are grinded against each other.

The comparison sample is γ-ray highly crosslinked (100 kGy) ultra high molecular weight polyethylene which manufactured by Kuanyue Biotechnology Co. Ltd and sold in the United States. A Concave-hemispherical hip joint with a diameter of 44.2 mm and a surface-roughened convex cobalt-chromium alloy hemispherical hip joint with a diameter of 44.0 mm are grinded against each other.

The wear medium is deionized water 632.4 ml/L, 367.6 ml/L bovine serum aqueous solution, EDTA 2.73 g/L, gentamicin 10 ml/L, and amphotericin 10 ml/L. The surface roughening of the cobalt-chromium alloy hemisphere is achieved by the process of reference 14. The polished cobalt-chromium alloy hemisphere is put into a tumbling ball mill with a rotation speed of 40 rpm and a ball milling time of 30 minutes. The ball milling medium is 500 ml of deionized water, 90 ml of alumina powder with a grain size of 500, and 200 ml of plastic with a grain size of SP2.

Experimental Group I: Preparation of Surface Super-Cross-Linked Ultra High Molecular Weight Polyethylene GUR1020E Compression molded and uncrosslinked ultra-high molecular weight polyethylene GUR1020E (that is, uncrosslinked ultra-high molecular weight polyethylene GUR1020 containing 0.1% by weight of Vitamin E) was produced by Orthoplastics, Ltd in the UK.

The molded rectangular bar was machined into ultra-high molecular weight polyethylene components: 65 mm×45 mm×8 mm flat plate, 65 mm×8 mm diameter flat plate or hemispherical cup with a diameter of 44.20 mm and a thickness of 4.5 mm.

The ultra-high molecular weight polyethylene components were placed on an aluminum plate then in a stainless steel container. The benzophenone powder (Benzophenone, Sigma-Aldrich, Reagent Plus®, 99%) was placed on the bottom of the container. The transparent glass lid was placed on top of the container. The container was vacuumed and filled in nitrogen. This vacuuming and Nitrogen filling was repeated for three times. Then the stainless-steel container was heated to the specified temperature and kept for a period, then cooled to room temperature.

The diffusion process was completed. After diffusion process, the ultra-high molecular weight polyethylene components were taken out and put into another stainless steel container. The vacuum and Nitrogen filling process was conducted three times. A UV light was shined through transparent glass lid on the benzophenone diffused surface of ultra-high molecular weight polyethylene with acetophenone. The average wavelength of the UV was about 365 nanometers, the UV radiation intensity was 175 mW/cm², and the radiation period was 60 minutes. FIG. 11 showed the radiation intensity of ultraviolet light change with the depth.).

Table 2 Various embodiments of benzophenone at different diffusion temperature and period of time

TABLE 2

| | Embodiment List | | | | | |
|---|---|---|---|---|---|---|
| | temperature | | | | | |
| period | 80° C. | 90° C. | 100° C. | 110° C. | 120° C. | 125° C. |
| 1 hour | | Embodiment II | Embodiment V | Embodiment VII | | |
| 1.5 hours | | Embodiment III | | | | |
| 2 hours | | Embodiment IV | Embodiment VI | Embodiment VIII | Embodiment IX | |
| 2.3 hours | | | | | Embodiment X | Embodiment XII |
| 4 hours | Embodiment I | | | | Embodiment XI | |

The weight per unit area of the surface layer of benzophenone diffused into the ultra-high molecular weight polyethylene GUR1020E was obtained by measuring the weight change of the flat or hemispherical cup before and after diffusion, and dividing the result by the exposed area (Table 3).

TABLE 3

The weight of benzophenone per unit area diffused into the surface layer of ultra high molecular weight polyethylene GUR1020E (Unit: mg/cm²)

|  | 80° C. | 90° C. | 100° C. | 110° C. | 120° C. | 125° C. |
|---|---|---|---|---|---|---|
| 1 hour |  |  | 0.981 (Embodiment V) | 1.908 (Embodiment VII) |  |  |
| 2 hours |  | 1.111 (Embodiment IV) | 2.010 (Embodiment VI) | 2.863 (Embodiment VIII) | 5.095 (Embodiment IX) |  |
| 2.3 hours |  |  |  |  | 6.810 (Embodiment X) | 7.360 (Embodiment XII) |
| 4 hours | 1.112 (Embodiment I) |  |  |  | 7.568 (Embodiment XI) |  |

It can be seen from Table 3 that the diffusion amount of benzophenone diffused into the surface layer of ultra-high molecular weight polyethylene GUR1020E per unit area was 1.112 mg/cm2 at the temperature of 80° C. in 4 hours. The diffusion amount of benzophenone diffused into the surface layer of ultra high molecular weight polyethylene GUR1020E per unit area rises to 7.568 mg/cm² if the temperature rises to 120° C. The amount of benzophenone diffused into the surface layer of ultra high molecular weight polyethylene GUR1020E per unit area decreased to 5.095 mg/cm² if the diffusion period is reduced to 2 hours. It can be seen that the temperature increased or the period prolonging are beneficial to the increase of benzophenone diffusion.

The surface-crosslinked component samples were immersed in acetone to remove unreacted benzophenone and soluble by-product of benzopinacol. The cleaned component samples were cut into 0.25 mm film by mechanical processing. Two-dimensional tensile mechanical properties test was performed according to the adjusted ASTM F F2977-13 method, and the final fracture force was measured as shown in Table 4. After calibration by the straight line in FIG. 9, the equivalent crosslinking degree was shown in Table 5.

TABLE 4

Two-dimensional tensile fracture force of 0.25 mm thick film on the surface of surface crosslinked ultra-high molecular weight polyethylene GUR1020E, unit: Newton

|  | 80° C. | 90° C. | 100° C. | 110° C. | 120° C. | 125° C. |
|---|---|---|---|---|---|---|
| 1 hour |  | 54.04 ± 4.32 | 59.96 ± 2.51 |  |  |  |
| 1.5 hours |  | 52.34 ± 1.96 |  |  |  |  |
| 2 hours |  |  | 57.2 ± 1.7 | 62.50 ± 2.50 | 67.19 ± 10.86 |  |
| 2.3 hours |  |  |  |  | 65.20 ± 3.50 | 69.35 ± 4.20 |
| 4 hours | 45.25 ± 2.38 |  |  |  |  |  |

TABLE 5

Equivalent crosslinking degree of 0.25 mm thick film on the surface of surface cross-linked ultra high molecular weight polyethylene, unit: kGy

|  | 80° C. | 90° C. | 100° C. | 110° C. | 120° C. | 125° C. |
|---|---|---|---|---|---|---|
| 1 hour |  | 185 ± 39 | 239 ± 23 |  |  |  |
| 1.5 hours |  | 170 ± 18 |  |  |  |  |
| 2 hours |  |  | 214 ± 15 | 266 ± 23 | 304 ± 98 |  |
| 2.3 hours |  |  |  |  | 286 ± 32 | 323 ± 38 |
| 4 hours | 106 ± 21 |  |  |  |  |  |

Table 4 and Table 5 Showed Following Results.

In embodiment 1, the final two-dimensional tensile fracture force of the 0.25 mm thick film on the surface of the surface crosslinked ultra-high molecular weight polyethylene GUR1020E was 45.25±2.38 Newtons, and the equivalent cross-linking degree is 106±21 kGy, which is not significantly different from the final breaking force (46.79±1.5 Newtons) of the 0.25 mm thick film of the commercial bulk high crosslinked ultra-high molecular weight polyethylene GUR020E by 100 kGy γ-ray (Mobile®, Table 6).

In embodiments II to XII, the 0.25 mm thick film of the surface crosslinked ultra-high molecular weight polyethylene GUR1020E has a two-dimensional tensile final fracture force between 52.34±1.96 Newton and 69.35±4.20 Newton, which have the equivalent cross-linking degree between 170±18 kGy and 323±38 kGy. These 52.34±1.96 Newton and 69.35±4.20 Newton were far higher than 46.79±1.5 (Table 6) of the commercial 100 kGy γ-ray bulk high crosslinking Mobile® Ultra high molecular weight polyethylene GUR020E.

TABLE 6

Two-dimensional tensile final fracture force and fracture toughness of a 0.25 mm thick film of commercial bulk high crosslinking ultra-high molecular weight polyethylene

| Material | GUR1020 | GUR1020 N2Vac® | GUR1020 Mobile® | GUR1020 X3® | GUR1020E Mobile® |
|---|---|---|---|---|---|
| γ ray, kGy | 0 | 30 | 75 | 90 | 100 |
| Post heat treatment | No | No | Re-melted | Annealed for three times | No |
| Final fracture force, Newtons | 28.75 ± 0.89 | 35.48 ± 1.08 | 48.17 ± 1.97 | 48.12 ± 1.37 | 46.79 ± 1.5 |
| Fracture toughness, Newton · mm | 103.2 ± 6.8 | 103.2 ± 6.8 | 144.8 ± 0.3 | 103.00 ± 6.6 | 104.3 ± 6.0 |

Figure 8:
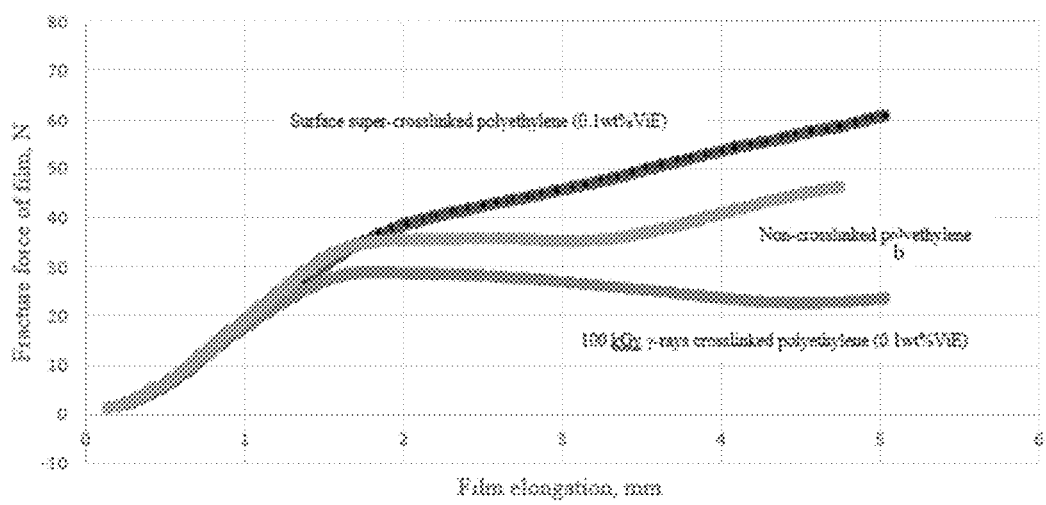
FIG. 8 shows the comparison of the load vs displacement curves. The upper curve is this invention (Embodiment 8, GUR1020E (0.1 wt % ViE)), the middle curve is 100 kGy γ-rays crosslinked ultra high molecular weight polyethylene GUR1020E (0.1 wt % ViE), and the lower curve is non-crosslinked ultra-high molecular weight polyethylene GUR1020.

By comparing Table 5 to Table 6, we can see that a 0.25 mm thick film of the surface super-cross-linking ultra-high molecular weight polyethylene (for example, embodiment VII), have much higher two dimensional tensile fracture force than the 0.25 mm thick film of the bulk highly crosslinked ultrahigh molecular weight polyethylene GUR1020 and GUR1020 E (75-100 kGy). The comparison results were shown in FIG. 8.

The ultra-high molecular weight polyethylene surface super-crosslinking of the present invention further extends to the depth, and the degree of crosslinking decays with the increase of the depth, showing the characteristics of gradient crosslinking.

Table 7 lists the changes in the two-dimensional tensile breaking force, equivalent crosslinking degree and fracture toughness of a 0.25 mm thick film of the ultra-high molecular weight polyethylene GUR1020E prepared in embodiment VI with the variation of depth. The equivalent cross-linking degree of the surface was 214±15 kGy, which is reduced to 99±11 kGy at 1.0 mm, 49±3 kGy at 1.5 mm, and finally 3±11 kGy at 2.5 mm (that is, non-crosslinked). This showed that the surface gradient crosslinking depth of the film was about 1.5 mm, of which the super crosslinking depth was about 1.0 mm, and the highly crosslinking depth was about 0.5 mm. Below 2.0 mm, the equivalent cross-linking degree was the transitioned to the range of traditional γ-ray sterilized ultra-high molecular weight polyethylene (0-40 kGy), and the total depth of surface gradient crosslinking was about 2.0 mm.

TABLE 7 the changes in the two-dimensional tensile fracture force, equivalent crosslinking degree and fracture toughness of a 0.25 mm thick film of the super-high molecular weight polyethylene GUR1020E prepared in embodiment 6 with the variation of depth.

| Depth, mm | 0 | 0.5 | 1 | 1.5 | 2 | 2.5 |
|---|---|---|---|---|---|---|
| fracture force, Newtons | 57.23 ± 1.66 | 51.47 ± 0.84 | 44.44 ± 1.17 | 38.92 ± 0.31 | 35.71 ± 1.19 | 33.84 ± 1.27 |

TABLE 7-continued the changes in the two-dimensional tensile fracture force, equivalent crosslinking degree and fracture toughness of a 0.25 mm thick film of the super-high molecular weight polyethylene GUR1020E prepared in embodiment 6 with the variation of depth.

| Depth, mm | 0 | 0.5 | 1 | 1.5 | 2 | 2.5 |
|---|---|---|---|---|---|---|
| Equivalent crosslinking degree. kGy | 214 ± 15 | 162 ± 8 | 99 ± 11 | 49 ± 3 | 20 ± 11 | 3 ± 11 |
| Fracture roughness, Newton · mm | 144.9 ± 12.6 | 140.7 ± 16.6 | 129.3 ± 12.1 | 119.7 ± 3.7 | 113.3 ± 5.2 | 116.4 ± 8.1 |

Figure 2:
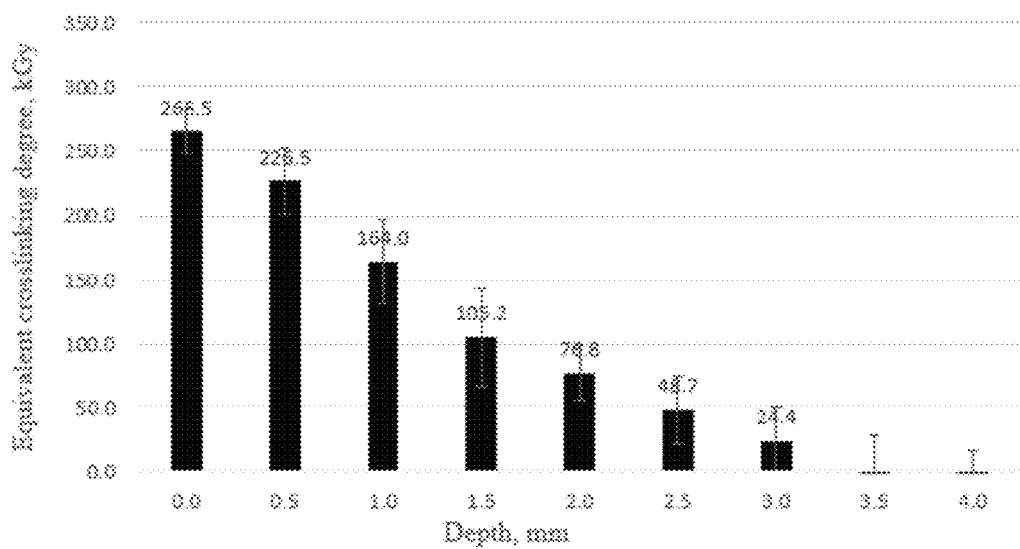
FIG. 2 shows equivalent crosslink degree relation to crosslinking depth of 0.25 mm films tested by small punch. The test samples were machined from surface super crosslinked ultra-high molecular weight polyethylene GUR1020 E (0.1 wt % viE) made by Embodiment 8.
Figure 3:
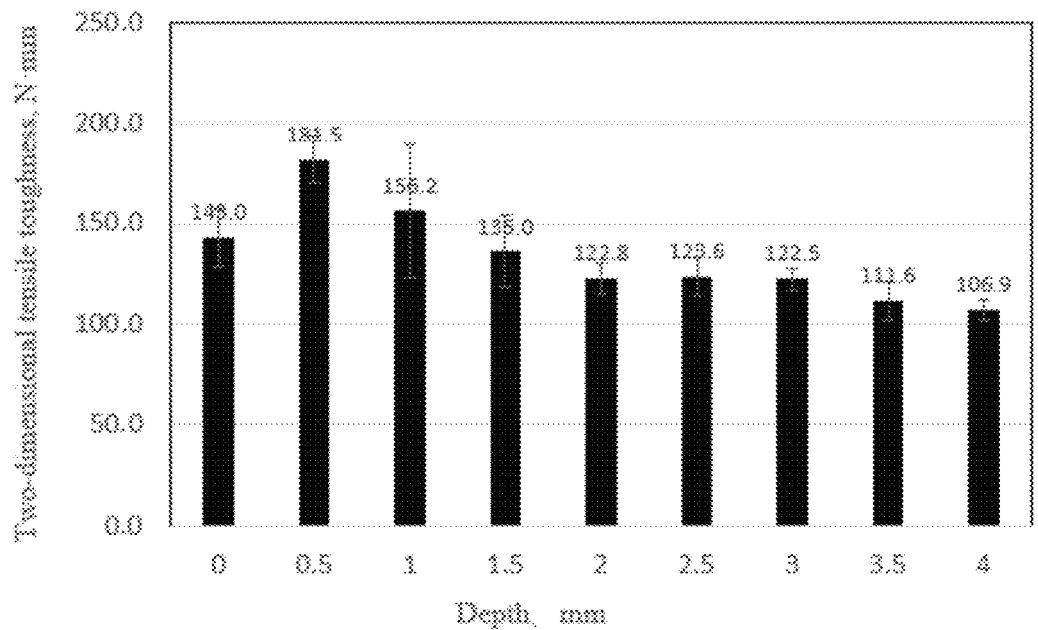
FIG. 3 shows work to failure relation to crosslinking depth of 0.25 mm films tested by small punch. The test samples were machined from surface super crosslinked ultra-high molecular weight polyethylene GUR1020 E (0.1 wt % viE) made by Embodiment 8.

The characteristics of the surface gradient crosslinking ultra-high molecular weight polyethylene GUR1020E prepared in embodiment VIII are shown in FIG. 1 and FIG. 2. The two-dimensional tensile fracture force of the top 0.25 mm thick film is as high as 62.50±2.50 Newtons, and the equivalent crosslinking degree is 262±23 kGy. Correspondingly, the thickness of the surface super crosslinked layer is increased to 1.5 mm, and the thickness of the highly cross-linked layer is about 1.0 mm, and below 2.5 mm, it will transitioned to low-level cross-linking or even non-cross-linking. The total depth of the gradient cross-linking of the ultra-high molecular weight polyethylene is about 3.0 mm.

Figure 6:
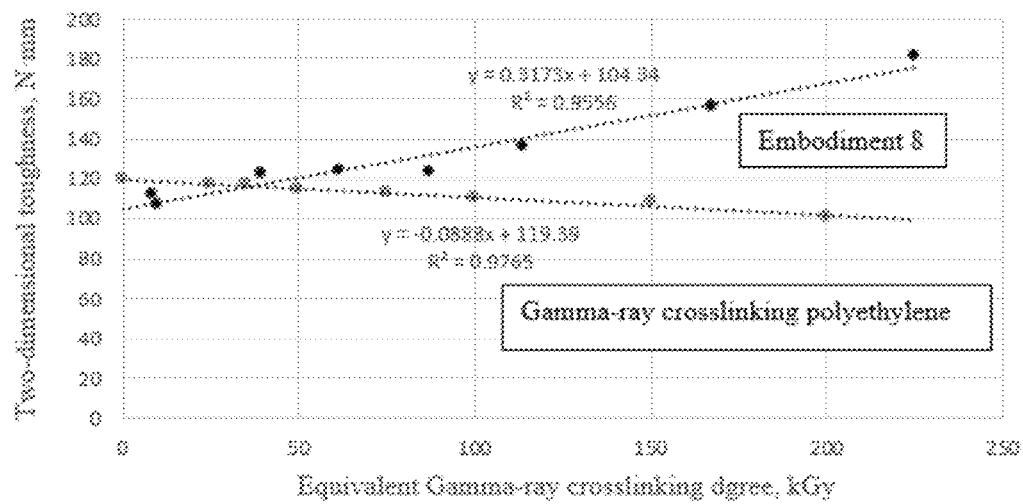
FIG. 6 shows a comparison diagram of work to failure vs equivalent crosslinking degree. The experimental data were from Embodiment 8. The comparative data were transformed to 0.25 mm film from original 0.5 mm film published by Masao Akagi, et al, J. Othop Res 24:2021-2027, 2006.

Surprisingly, for the surface super-crosslinked ultra-high molecular weight polyethylene GUR1020E film of the present invention, the change of the fracture toughness with depth is the same as that of the equivalent crosslinking degree with depth (shown in FIG. 2, FIG. 3, and Table 7). As further shown in FIG. 6, the fracture toughness of the surface super-crosslinked ultra-high molecular weight polyethylene GUR1020E film made by the method described in embodiment VIII is proportional to the equivalent cross-linking degree, while the fracture toughness of the conventional gamma-ray bulk cross-linked ultra-high molecular weight polyethylene film has an inversely proportional to equivalent cross-linking degree. Here, the data of γ-ray crosslinked polyethylene is taken from the 0.50 mm film test results of M. Akagi et al., J. Othop Res 24: 2021-2027, 2006, and converted into 0.25 mm film fracture toughness. It may be because that the main chain of the surface super crosslinked super-high molecular weight polyethylene of the present invention is cross-linked and the side chains are not broken; while the traditional I-ray cross-linked ultra high molecular weight polyethylene has crosslinked main chains but also broken some side chains as well, so that the traditional γ-ray cross-linked ultra high molecular weight polyethylene under two-dimensional stretching at low dose (0-100 kGy), has a fracture force increasing linearly with the increasing of γ dose, but to the high dose (100-250 kGy), the fracture force remains basically the same, and the degree of crosslinking does not increase any more (Table 8, and FIG. 10).

TABLE 8 two-dimensional tensile fracture force and fracture toughness of 0.25 mm thick film of γ -ray bulk crosslinked ultra high molecular weight polyethylene as a function of γ -ray crosslinking dose

| γ dose, kGy | 0 | 30 | 50 | 100 | 150 | 200 | 250 |
|---|---|---|---|---|---|---|---|
| GUR1020 E Fracture force, Newton | 32.53 ± 0.74 | 34.99 ± 0.96 | 38.30 ± 1.50 | 46.79 ± 1.67 | 50.19 ± 2.07 | 53.97 ± 3.33 | 59.74 ± 2.73 |
| GUR1020 Fracture force, Newton | 28.75 ± 0.89 | 33.81 ± 1.04 | 35.94 ± 1.64 | 48.12 ± 1.37 | 51.51 ± 1.40 | 53.79 ± 3.50 | 53.38 ± 5.71 |
| GUR1020E fracture roughness, Newton · mm | 113 ± 5 | 103 ± 4 | 100 ± 5 | 126 ± 37 | 112 ± 30 | 118 ± 20 | 137 ± 16 |
| GUR1020 fracture roughness, Newton · mm | 103 ± 7 | 83 ± 4 | 83 ± 7 | 126 ± 37 | 113 ± 11 | 123 ± 25 | 103 ± 42 |

Figure 12:
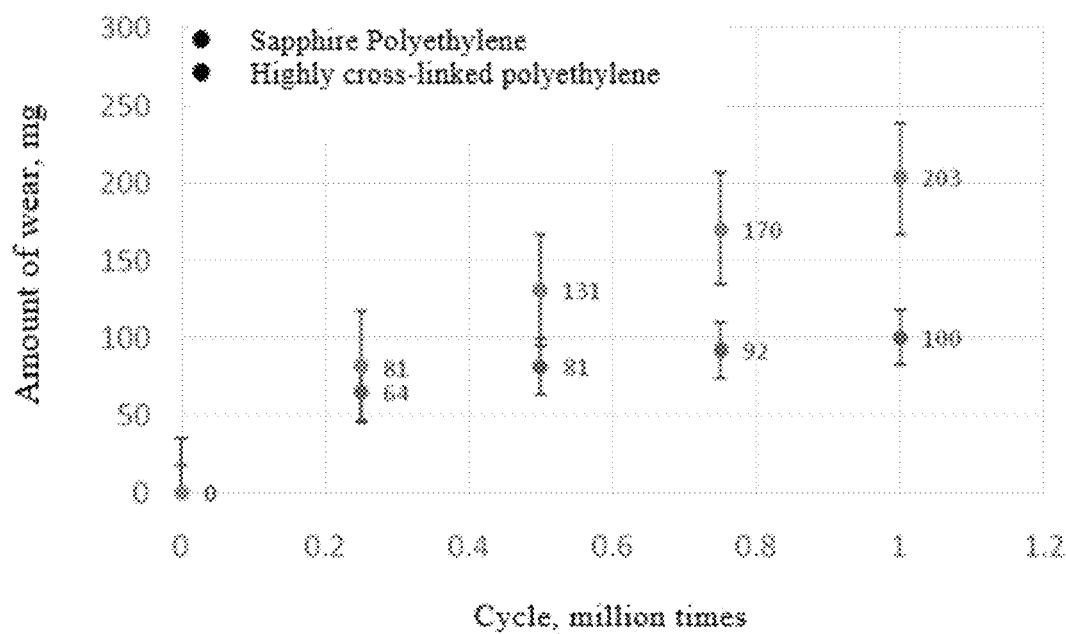
FIG. 12 shows the comparison of the wear test results of 44 mm diameter hip joints. The low-wear curve represents the surface super-crosslinked ultrahigh molecular weight polyethylene GUR1020E (0.1% wt ViE) of the present invention, and the high-wear curve represents the gamma-ray highly crosslinked (100 kGy) ultra-high molecular weight polyethylene GUR1020E (0.1% wt ViE). The counter surface was CoCr heads which were intensively roughened.

FIG. 12 shows wear test results comparison of two hips with a diameter of 44 mm made by the method of the present application and the prior art respectively, that is, the test results of the surface super-crosslinked ultra-high molecular weight polyethylene GUR1020E of the present invention and 100 kGy gamma ray highly crosslinked ultra-high molecular weight polyethylene are wear against the roughened cobalt-chromium alloy. The surface super cross-linked ultra-high molecular weight polyethylene GUR1020E made by the method described in embodiment VIII has a lower worn loss than the gamma ray highly crosslinked (100 kGy) ultra-high molecular weight polyethylene GUR1020E, when wear against roughened cobalt-chromium alloy under the same conditions. After one million cycles, the worn loss of the surface super crosslinked ultra-high molecular weight polyethylene GUR1020E of the present invention is 1.0 time lower than that of the 100 kGy gamma ray highly cross-linked ultra-high molecular weight polyethylene GUR1020E.

The experimental data in FIG. 12 is mathematically simulated, the relationship between the worn loss (W) and the number of cycles (C) of the surface super-cross-linked ultra-high molecular weight polyethylene GUR1020E of the present invention is: $W=(99\pm16)(C)^{1/(3.14\pm0.05)}$. According to the above formula, it can be deduced that the worn loss of the surface super-cross-linked ultra-high molecular weight polyethylene GUR1020E of the present invention is 1.6 times and 2.0 times lower than that of the GUR1020E which is highly crosslinked (100 kGy) by γ-ray.

Reference 14 publishes the results of Streitech's 40 mm X3® w against the roughened cobalt-chromium alloy. After one million cycles and two million cycles, the worn loss of X3® is 260-60 mg and 400±80 mg, while the worn loss of the super-high molecular weight polyethylene GUR1020E of the surface of the invention is 99±16 mg and 124±20 mg, so the worn loss of the surface super-crosslinked ultra-high molecular weight polyethylene GUR1020E of the present invention is 1.6 times and 2.2 times lower wear than that of X3®. The higher the number of cycles, the greater the difference in worn loss. It can be seen that the present invention has achieved significant technical progress. Moreover, the ultra-low worn loss of the present invention is also unprecedented, which is unexpected.

Experimental Group 2: Preparation of Surface Super-Cross-Linked Ultra High Molecular Weight Polyethylene GUR1020

The surface super-cross-linking ultra high molecular weight polyethylene of GUR1020 is prepared and the same procedure of GUR1020E are shown in experimental group 1. The diffusion condition of GUR1020 and GUR1020E is 110° C. for 3.0 hours; the cross-linking condition of GUR1020 and GUR1020E is ultraviolet irradiation at 175 mW/cm$^2$ for 1.0 hour.

Results: a surface layer of 0.25 mm film of the surface super-cross-linked ultra high molecular weight polyethylene GUR1020E has a two-dimensional tensile mechanical fracture force of 54.3±1.2 N and an equivalent cross-linking degree of 187 kGy. A surface layer of 0.25 mm film of the super-cross-linked ultra-high molecular weight polyethylene GUR1020 has a two-dimensional tensile mechanical final fracture force of 55.2±3.91 N, and an equivalent cross-linking degree of more than 100 kGy.

It can be seen that after the two substrates are processed under the same conditions, the difference in the two-dimensional tensile mechanical fracture force is within the standard deviation range. Therefore, the diffusion and cross-linking method of the present invention is also applicable to the ultra-high molecular weight polyethylene GUR1020 that does not contain an oxidant.

Comparative Experiment

The comparative experiment was performed referring to embodiment 1 in CN102276864 and U.S. Pat. No. 9,828,474.

This comparative experiment group uses two kinds of substrates: one substrate is N2Vac® ultra high molecular weight polyethylene (GUR1020), prepared according to the method of U.S. Pat. No. 5,414,049, and cross-linked by 30.9 kGy γ-ray in a nitrogen atmosphere; the other substrate was X3® ultra high molecular weight polyethylene (GUR1020), which was prepared according to the method of U.S. Pat. No. 7,517,919, is radiated by about 30 kGy γ-ray and annealed at 130° C. for three times in a nitrogen atmosphere. Both substrates are 65 mm×45 mm×8 mm flat plates. The plate was immersed in 11.1 mg/ml benzophenone solution, taken out after one minute, and dried in air at room temperature, so that the surface coating of benzophenone is finished.

Then the weight change before and after coating the substrate was weighed with an electronic balance with a precision of 0.1 mg, recorded, and divided by the total surface area of the plate to obtain the coating weight per unit area. The weight gain of the N2Vac® and X3® plate was 0.00688 mg/cm$^2$, which is about one thousandth of the benzophenone diffusion amount in the experimental group of the present invention (shown in Table 3).

A glass beaker was filled with deionized water, nitrogen bubbles was passed in the water, and oxygen in the water was removed, and the water was heated to 65° C. The ultra-high molecular weight polyethylene substrate coated with benzophenone was connected to a stainless steel sheet. The ultra-high molecular weight polyethylene sank on the bottom of the glass due to gravity, and the surface is submerged by the water. The surface crosslinking was conducted for the ultra-high molecular weight polyethylene substrate by exposing ultraviolet light at an average wavelength of 365 nanometers, the intensity of 52 mW/cm$^2$ for the period of 1 hour. The surface cross-linked ultra-high molecular weight polyethylene is washed with acetone and water, mechanically processed, and 0.25 mm films are taken layer by layer from the cross-linked surface for two-dimensional tensile mechanical property testing.

Figure 4:
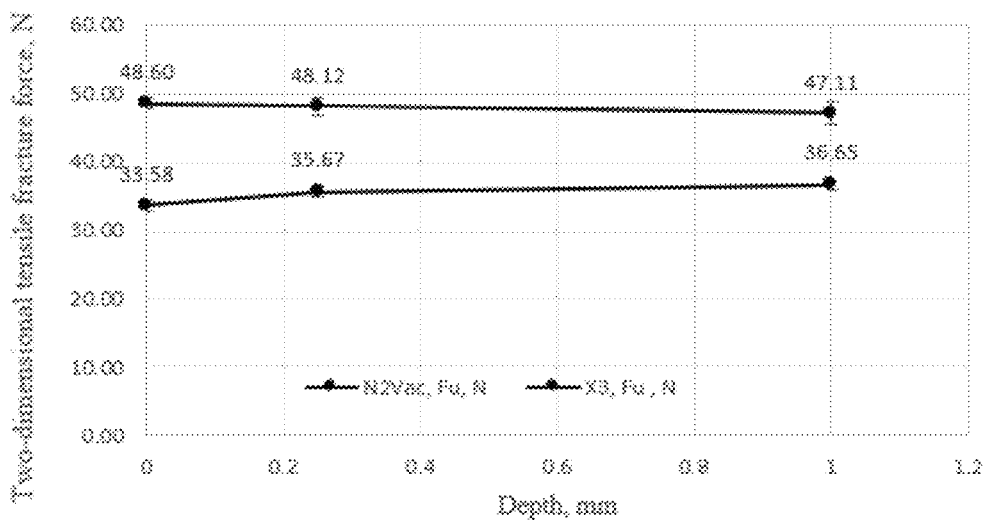
FIG. 4 shows ultimate load relation to crosslinking depth of 0.25 mm films tested by small punch. The test samples were machined from surface crosslinked ultra-high molecular weight polyethylene GUR1020 made by the process of CN102276864, U.S. Pat. No. 9,132,209.
Figure 5:
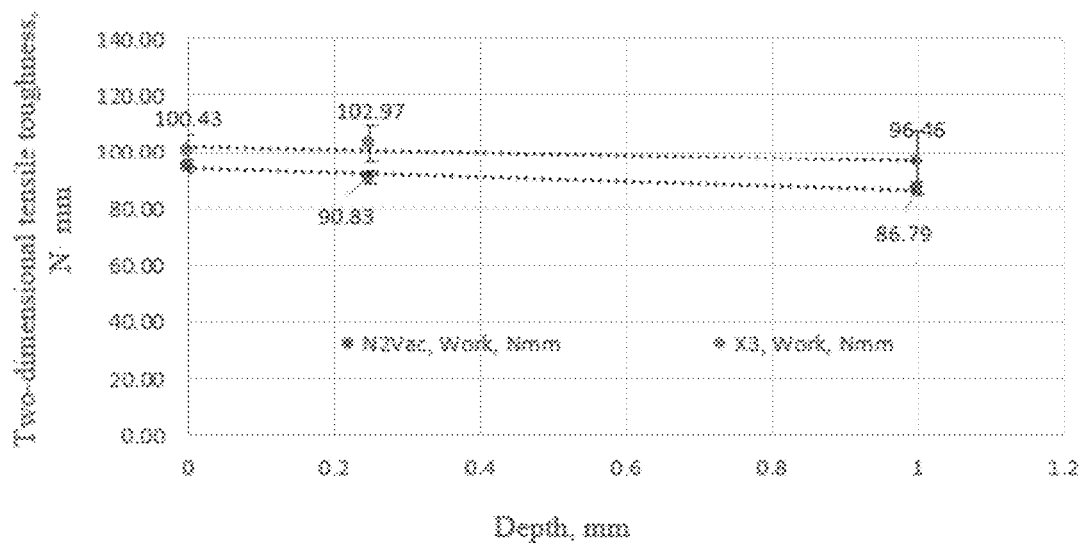
FIG. 5 shows work to failure relation to crosslinking depth of 0.25 mm films tested by small punch. The test samples were machined from surface crosslinked ultra-high molecular weight polyethylene GUR1020 made by the process of CN102276864, U.S. Pat. No. 9,132,209.

FIG. 4 shows the relationship between the two-dimensional tensile fracture force and the cross-linking depth of 0.25 mm film of the surface cross-linked X3® and N2Vac® obtained in the comparative experiment. Wherein the two-dimensional tensile fracture force of 0.25 mm film of X3® was 48.6 Newtons, the two-dimensional tensile fracture force of 0.25 mm film of N2Vac® is 33.58 Newtons. According to the relationship between the two-dimensional tensile fracture force of ultra-high molecular weight polyethylene GUR1020 and the degree of crosslinking (FIG. 10), the crosslinking degree corresponding to X3® is 100 kGy, and the crosslinking degree corresponding to N2Vac® is 30 kGy.

FIG. 4 shows that the two-dimensional tensile fracture force of the 0.25 mm film of the surface cross-linked X3® and N2Vac® obtained from the comparative experiment does not change with crosslinking depth. This means that the thickness of the surface crosslinking obtained by this method is extremely thin and is not greater than 0.25 mm.

FIG. 5 shows the relationship between the two-dimensional tensile fracture toughness of the surface cross-linked X3® and N2Vac® 0.25 mm films obtained from the comparative experiment and the cross-linking depth. The trend is the same as that in FIG. 4. The tensile fracture toughness of the surface is basically the same as that in the bulk, and the highest value is about 100 Newton millimeters. It is further explained that the thickness of the surface cross-linking in this method is extremely thin and is not greater than 0.25 mm.

SUMMARY

Table 9 lists the comparison between the surface super crosslinked ultra-high molecular weight polyethylene obtained by the method of the present invention and the surface crosslinked ultra-high molecular weight polyethylene obtained by the comparative method (referring to embodiment 1 of CN102276864 and U.S. Pat. No. 9,828,474).

TABLE 9

|  | Photoinitiator | UV intensity | Surface super crosslinking depth | Worn loss result |
|---|---|---|---|---|
| The method of this invention | Diffusion at high temperature >0.9 mg/cm$^2$ | >100 mW/cm$^2$ | >1.0 mm | Rough surface test |
| Comparative method | Coating at room temperature 0.006 mg/cm$^2$ | <100 mW/cm$^2$ | <0.25 mm | Smooth surface test |

Firstly, the diffusion process of the present invention was conducted at a high-temperature (>50° C.), which allows photoinitiator (such as benzophenone) to penetrate into the deeper surface layer of ultra-high molecular weight polyethylene, and the depth can reach 3.0 mm. In contrast, the comparative method of pre-arts was a coating process conducted at room temperature, the photoinitiator was introduced only on the top surface, the depth of penetration into the substrate is less than 0.25 mm (FIGS. 4 and 5) and the coating of the photoinitiator is small (about 0.006 mg/cm$^2$).

Secondly, high-intensity ultraviolet (>100 mW/cm$^2$) irradiation was used in the cross-linking process of the present invention, while low-intensity ultraviolet (<100 mW/cm$^2$) irradiation was used in the comparative method of the pre-arts. Deep cross-linking of the present invention occurred because high-intensity ultraviolet radiation induced deep-diffused photoinitiators to react with ultra-high molecular weight polyethylene. In the present invention, the depth of surface super crosslinking was greater than 1.0 mm, while in the comparative method, the depth was less than 0.25 mm.

Finally, the surface-crosslinked ultra-high molecular weight polyethylene of the present invention used the roughened cobalt-chromium alloy balls for the wear experiment; while the surface-crosslinked ultrahigh molecular weight polyethylene of the comparative method adopted the polished Cobalt-chromium alloy balls for the wear test. The experimental conditions of the present invention were more challenging and closer to extreme clinical conditions.

All documents mentioned in the present invention are cited as references in this application, just as each document is individually cited as a reference. In addition, it should be understood that after reading the above teaching content of the present invention, those skilled in the art can make various changes or modifications to the present invention, and these equivalent forms also fall within the scope defined by the appended claims

REFERENCES

1. J. Caitlin, et al, "The effect of radiation dose on the tensile and impact toughness of highly crosslinked and remelted ultrahigh-molecular weight polyethylenes", J. Biomed. Mat. Res, Vol. 97B, No. 2, p 327-333.
2. U.S. Pat. No. 6,494,917.
3. Ebru Oral, et al, "Surface Cross-Linked UHMWPE Can Enable the Use of Larger Femoral Heads in Total Joints", Orthop Res 31:59-66 (2013).
4. CN 102276864.
5. U.S. Pat. No. 9,132,209.
6. U.S. Pat. No. 9,951,190.
7. ASTM F 2977-13, "Standard Test Method for Small Punch Testing of Polymeric Biomaterials Used in Surgical Implants".
8. Jacob Blitz et al, "FEA based DOE study solves specimen slippage in thin film small punch test of highly cross-linked UHMWPE", ORS 2016 Annual Meeting Poster No. 1966.
9. Yu Lei Dong, et al, "Ceramics on Ceramics or Ceramics on polyethylene for Total Hip Arthroplasty: A Systemic Review and Meta analysis of Prospective Randomized Studies". Chinese Medical Journal|May 5|Volume 128|Issue 9, p 1223-1231.
10. Jöm Reinders, et al, "Wear Performance of Ceramics-On-Metal Hip Bearings", PLOS ONE|www.plosone.org, August 2013|Volume 8|Issue 8|e73252.
11. Korduba L A, et al, "Method creating abrasive components for wear testing", Poster No. 2290, 55$^{th}$ Anneal meeting of the orthopedic research society.
12. US2016/0250779 A1.

The invention claimed is:

1. A crosslinking method for a surface layer of an ultra-high molecular weight polyethylene substrate, wherein the crosslinking method includes:
   (1) providing a photoinitiator in the ultra-high molecular weight polyethylene substrate, and diffusing the photoinitiator from a surface of the substrate into the surface layer of the ultrahigh molecular weight polyethylene substrate at a temperature above the melting point of the photoinitiator and below the melting point of the ultra-high molecular weight polyethylene;
   (2) exposing the diffused surface layer with ultraviolet light to crosslink the surface layer, thereby forming a surface layer gradient crosslinked ultra-high molecular weight polyethylene, wherein a radiation intensity of the ultraviolet light is ≥100 mW/cm$^2$.

2. The crosslinking method according to claim 1, wherein the ultra-high molecular weight polyethylene substrate is non-ionized crosslinked ultra-high molecular weight polyethylene.

3. The crosslinking method according to claim 1, wherein the surface layer of ultra- high molecular weight polyethylene substrate is a bearing surface layer for a medical implant.

4. The crosslinking method according to claim 1, wherein the ultra-high molecular weight polyethylene includes an antioxidant.

5. The crosslinking method according to claim 4, wherein the antioxidant is one or more selected from the following group: Vitamin E, Tetrakis[methylene(3,5-di-tert-butylhydroxyhydrocinnamate)]methane, Thiodiethylene bis[3-[3,5-di-tert-butyl-4-hydroxyphenyl]propionate], Octadecyl 3,5-di-tert-butyl-4-hydroxylhydrocinnamate, N,N'-hexane-1,6-diylbis(3-(3,5-di-tert-butyl-4-hydroxyphenylpropionamide)), Benzenepropanoic acid, 3,5-bis(1,1-dimethyl-ethyl)-4-hydroxy-C7-C9 branched alkyl esters, 1,3,5-TRis(3,5-di-tert-butyl-4-hydroxybenzyl)-2,4,6-trimethylbenzene, 2,4-bis(dodecylthiomethyl)-6- methylphenol, Triethylene glycol bis(3-tert-butyl-4-hydroxy-5-methylphenyl)propionate, 2,2'-methylenebis(4-methyl-6-tert-butylphenol)monoacrylate, 1,3,5-TRis(3,5-di-tert-butyl-4-hydroxybenzyl)-1,3,5-triazine-2,4,6(1H,3H,5H)-trione, Benzenamine,N-phenyl-,reaction products with 2,4,4-trimethylpentene, 2,4-bis(octylthio)-6-(4-hydroxy-3,5-di-tert-butylanilino)-1,3,5-triazine, 5,7-di-t-butyl-3-(3,4 di-methylphenyl)-3H-benzofuran-2-one, Tris(2,4-di-tert-butylphenyl)phospite and Pentaerythritol tetra [3- (3,5-di-tert-butyl-4-hydroxyphenyl) propionate].

6. The crosslinking method according to claim 4, wherein the antioxidant is Vitamin E.

7. The crosslinking method according to claim 4, wherein the content of antioxidant is 0.01-0.20% by weight.

8. The crosslinking method according to claim 4, wherein the content of antioxidant is 0.01-0.10% by weight.

9. The crosslinking method according to claim 1, wherein the photoinitiator is one or more selected from the following groups: benzophenone, 4-chlorobenzophenone, 2-chlorobenzophenone, 4,4' dichlorobenzophenone, 2-methylanthraquinone, 2-ethylanthraquinone, 2-chloroanthraquinone, p-chloro Anthraquinone, benzyl sulfide, benzyl sulfoxide, phenyl sulfoxide, 4-acetylbiphenyl, anthrone, and hexachlorobenzene.

10. The crosslinking method according to claim 1, wherein the photoinitiator is benzophenone.

11. The crosslinking method according to claim 1, wherein in (1), the diffusion temperature is 50° C-134° C.

12. The crosslinking method according to claim 1, wherein in (1), the diffusion temperature is 81° C-130° C.

13. The crosslinking method according to claim 1, wherein the total depth of the surface layer gradient crosslinking is 3.5 mm.

14. The crosslinking method according to claim 1, wherein the depth of the surface super crosslinked layer is 0.5-1.5 mm.

15. The crosslinking method according to claim 1, wherein the diffusion amount of the photoinitiator is greater than 0.9 mg/cm$^2$.

* * * * *